(12) United States Patent
Soukup

(10) Patent No.: US 8,703,976 B2
(45) Date of Patent: Apr. 22, 2014

(54) MANUFACTURING PROCESS FOR 8-ARYLOCTANOIC ACIDS SUCH AS ALISKIREN

(75) Inventor: Milan Soukup, Sarasota, FL (US)

(73) Assignee: Milan Soukup, Sarasota, FL (US)

( * ) Notice: Subject to any disclaimer, the term of this patent is extended or adjusted under 35 U.S.C. 154(b) by 0 days.

(21) Appl. No.: 13/337,071

(22) Filed: Dec. 24, 2011

(65) Prior Publication Data

US 2012/0296100 A1 Nov. 22, 2012

Related U.S. Application Data

(60) Provisional application No. 61/542,243, filed on Oct. 2, 2011.

(51) Int. Cl.
C07D 307/00 (2006.01)
(52) U.S. Cl.
USPC .......................................................... 549/321
(58) Field of Classification Search
USPC .......................................................... 549/321
See application file for complete search history.

(56) References Cited

U.S. PATENT DOCUMENTS

| 5,559,111 A * | 9/1996 | Goschke et al. .......... 514/227.5 |
| 2011/0092706 A1 | 4/2011 | Soukup |
| 2011/0105767 A1 | 5/2011 | Soukup |
| 2011/0137047 A1 | 6/2011 | Soukup |

FOREIGN PATENT DOCUMENTS

| CA | CA 2 634 513 A1 | 12/2009 |
| EP | 0 678 503 B1 | 10/1995 |
| EP | 0678503 B1 | 10/1995 |
| EP | 1215201 B1 | 6/2002 |
| EP | 1 958 666 A1 | 8/2008 |
| EP | 1958 666 A1 | 8/2008 |
| EP | 2 062 874 | 5/2009 |
| EP | 2 189 442 A1 | 5/2010 |
| GB | 2 431 640 A | 5/2007 |
| GB | 2 431 641 A | 5/2007 |
| GB | 2 431 642 A | 5/2007 |
| GB | 2 431 643 A | 5/2007 |
| GB | 2 431 644 A | 5/2007 |
| GB | 2 431 645 A | 5/2007 |
| GB | 2 431 646 A | 5/2007 |
| GB | 2 431 647 A | 5/2007 |
| GB | 2 431 648 A | 5/2007 |
| GB | 2 431 649 A | 5/2007 |
| GB | 2 431 650 A | 5/2007 |

(Continued)

OTHER PUBLICATIONS

H. Ruger et al. Tetrahedron Letters, 2000, 41, 100085. D.A. Sandham et al. Tetrahedron Letters, 2000, 41, 10091.
A. Dondoni et al. Terahedron Letters, 2001, 42, 4819.
Drugs future, 2001, 26(12).
S. Henessian et al. J. Org. Chem. 2002, 67, 4261.

(Continued)

*Primary Examiner* — Janet L Andres

(57) ABSTRACT

The present invention relates to a novel manufacturing process and novel intermediates useful in the synthesis of pharmaceutically active compound such as Aliskiren.
The invention describes preparation of enantiomerically pure 8-aryloctanoic acid of formula I from a chiral compound of formula IV. Friedel-Crafts reaction of this compound of formula IV with a compound of formula III provides compound of formula II which is converted reductively in a few steps into the compound of formula V, a know intermediate in the synthesis of compound of formula I. According to the disclosed process, Aliskiren can be now prepared from commercial starting materials (Guajacol or 2-bromoanisole, cis- or trans-1,4-dichloro-2-butene and 4(S)-benzyl-3-isovaleroyl-oxazolidin-2-one) in less than 8 process steps.

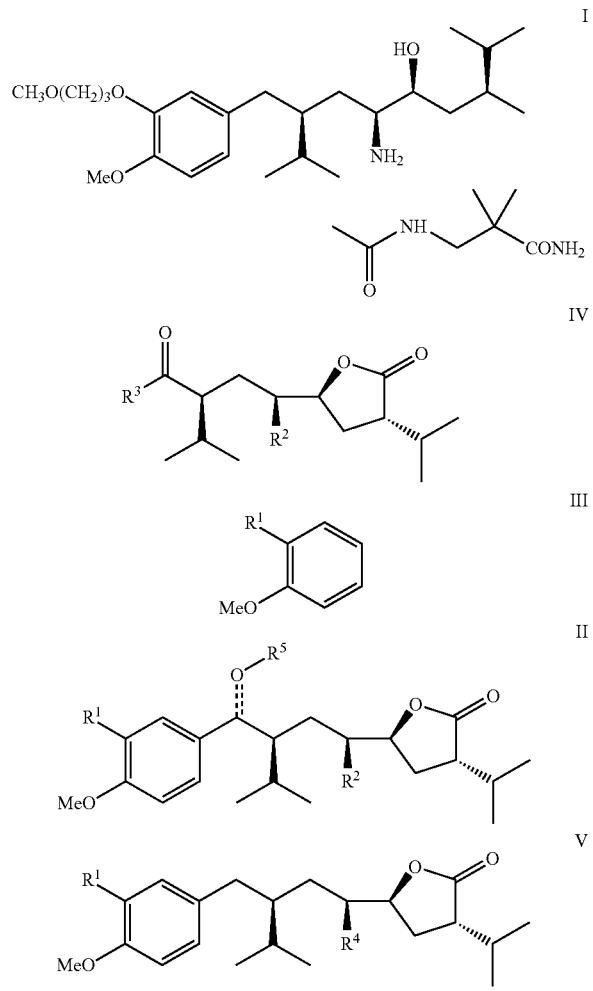

20 Claims, No Drawings

(56) References Cited

FOREIGN PATENT DOCUMENTS

| | | |
|---|---|---|
| GB | 2 431 651 A | 5/2007 |
| GB | 2 431 652 A | 5/2007 |
| GB | 2 431 653 A | 5/2007 |
| GB | 2 431 654 A | 5/2007 |
| WO | WO01/09079 A1 | 2/2001 |
| WO | WO01/09083 A1 | 2/2001 |
| WO | WO02/02487 A1 | 1/2002 |
| WO | WO02/02500 A1 | 1/2002 |
| WO | WO 02/02500 A1 | 1/2002 |
| WO | WO02/02508 A1 | 1/2002 |
| WO | WO02/08172 A1 | 1/2002 |
| WO | WO 02/092828 A2 | 11/2002 |
| WO | WO 03/103653 A1 | 12/2003 |
| WO | WO 2005/090305 A1 | 9/2005 |
| WO | WO2006/024501 A1 | 3/2006 |
| WO | WO2006/095020 A1 | 9/2006 |
| WO | WO 2006/131304 A2 | 12/2006 |
| WO | WO 2007/006532 A1 | 1/2007 |
| WO | WO2007/054254 A1 | 3/2007 |
| WO | WO2007/039183 A1 | 4/2007 |
| WO | WO2007/045420 A2 | 4/2007 |
| WO | WO2007/048620 A1 | 5/2007 |
| WO | WO2007/118681 A1 | 10/2007 |
| WO | WO2008/119804 A1 | 10/2008 |
| WO | WO2008/155338 A2 | 12/2008 |
| WO | WO2009/049837 | 4/2009 |
| WO | WO2009/049837 A2 | 4/2009 |
| WO | WO2010/010165 | 1/2010 |
| WO | WO2010/010165 A1 | 1/2010 |
| WO | WO2010/112482 | 10/2010 |
| WO | WO2011/019789 | 2/2011 |
| WO | WO2011/064790 | 6/2011 |
| WO | WO2011/082506 | 7/2011 |
| WO | WO2011/082806 | 7/2011 |

OTHER PUBLICATIONS

R. Goschke et al. Helv. Chim. Acta 2003, 86, 2848.
Hua Dong et al. Tetrahedron Letters 2005, 46, 6337.
K.B. Lindday et al. J. Org. Chem. 2006, 71, 4766.
J.A. Boogers et al. Org. Process &Develop. 2007, 11, 585.
A. Andrusko et a. Tetrahedron letters 2008, 49, 5980.
TCI Reagent Gude 2009-2010, 50-66 16-17 85-89 90-93.
J. Advanced Org. Chem. J Wiley&sons NY 1991, p. 1209-1211.
Hoben-Weyl, Methoden der Org. Chemie, 4th Ed., Synthese von Peptidenl, vol. 15/II (1974), vol. IX (1955), vol. E11 (1985), Thieme Verlag.
E.Gross The Peptides, vol. 1 and 2, Academic Press. London 1970/80.
M.Bohdansky,Princelpes of Peptide Synthesis, Springer Verlag, Berlin 1984.
N.J. Manesis et al. J. Org. Chem. 1987, 52, 5331.
M. Kim et al. Archiv of Pharm. Res. 2004, 27, 151.
D.J. Ager etal. Org. Process Res. & Develop. 2004, 8, 72.
J. Kaiser et al. Microbiol. Rev. 1966, 60(3), 483.
D. Billeret et al. J. Heterocycl. Chem. 1993, 30, 671.
W. Greene et al. Protective Groups in org. Synthesis, 3rd Ed. J. Wiley&Sons 1999, p. 17-245, 494-653.
Ch.T. West et al., J. Org. Chem. 1973, 38, 2675.
J. Fry et al. J Org. Chem. 1978, 43, 374.
G. Olah, et al. Synthesis, 1986, 770.
A. On et al. Synthesis, 1987, 736.
H. Firouzabadi et al. Tetrahedron 2004, 60, 10843.
H. Fillon et al. Tetrahedron 2003, 59, 8199.
G.A.Kraus et al. Tetrahedron letters 2002, 43, 7077.
S. Repichet et al. Tetrahedron Letters, 2003, 44, 2037.
K. Kageyama et al. J. Org Chem. 1975, 40, 1932.
J. Vekemans et al. J. Org. Chem. 1990, 55, 5336.
J. Sauter et al., JACS 1959, 81, 3677.
J. Sauter et al. JACS 1959, 81, 3881.
M. Shah et al. Tetrahedron Letters 1986, 27, 5437.
E,J; Corey et al. Tetrahedron letters 1980, 21, 1819.
P.A. Evans et al. Tetrahedron Letters 1999, 40, 1253.
P.A. Evans et al. Tetrahedron Letters 1997, 38, 5249.
M. Maier et al. Synlett 1995, 1029.
H. Sheldrake et al. Org. Biomol. Chem. 2009, 7, 205.
S. Behr et al. Eur. J. Org Chem. 2004, 3884.
M.T. Barros et al. Tetrahedron 2009, 65, 396.
J.M.Holland et al. J. Org. Chem. 2003, 68, 747.
T.J. Donohoe et al. Org. Lett. 2009, 11, 2305.
S. Nahm et al. Tetrahedron Letters 1981, 22, 3815.
J.A. Murphy et al. Org. Letters 2005, 7, 1427.
R. Chenevert et al. J. Org. Chem. 1996, 61, 1219.
E. Vedejs et al. J. Am. Chem. Soc. 1996, 1809.
S. Henessian et al. Org. Lett. 2010, 12, 1816.
P. Herold et al. J. Org. Chem. 1989, 54, 1178.
M.E.Mayer et al. Liebigs Ann. Chem. 1990, 323.
J.Beger J. Prakt. Chem. 1991, 333, 677.
P.A. Wehrli J. Org. Chem. 1977, 42, 2939.
J.E. Bordwell at al. J. Org. Chem. 1963, 28, 1765.
N.S.Zefirov et al. J. Org. Chem. 1982, 47, 3679.
T. Sugiyama Bull. Inst. Chem. Res. Kyoto Univ. 1989, 67, 112.
M. Inoue et al. J. Heterocycl. Chem. 1984, 21, 725.
A.J. Bloom et al. Tetrahedron Letters 1986, 27, 873.
W.W.Zajac et al. J. Org. Chem. 1986, 51, 2617.
A. Inoue et al.J. Org. Chem. 2001, 66, 4333.
Y. Goldberg et al. tetrahedron 1990, 46, 1911.
K. Haffner et al. Tetrahedron Letters 1964, 52, 3953.
H. Nozaki Can. J. Chem. 1968, 46, 3333.
C. Berse et al. Can. J. Chem. 1971, 49, 2610.
H. Aray et al. Tetrahedron Lett. 2009, 50, 3329.
F. Pesciaioli et al. Angew. Chem. Int. 2008, 47, 8703.
S. Fiaravanti et al. J. Org. Chem. 2005, 70, 3296.
K. Guthikonda et al. 2002, 124, 13672.
M.E. Tanner et al. Tetrahedron lett. 1994, 35, 4073.
G.A.Klau et al. Terahedron Lett. 2002, 43, 7077.
M.Kawamura et al. Tetrahedron 2006, 62, 9201.
M.Yato et al. Heterocycles 1998, 49, 233.
D.V. Nadkarni et al. Org. Proc.Res.&Develop. 2008, 12, 1142.
A.Kamal et al. Terahedron Lett. 1997, 39, 6945.
H. Bayley et al. Tetrahedron Lett. 1978, 39, 3633.
H.S.Prakash et al. Syn Commun. 1994, 24, 549.
K.Purushothoma et al. Synlett 2000, 5, 683.
N.Bensel et al. Tetrahedron Lett. 2002,43,4281.
S.Gowrisankar et al. JACS 2010, 132,11592.
D.Nobel Chem Commun. 1993, 419.
J.Nui et al. JACS 2009, 74,5075.

* cited by examiner

MANUFACTURING PROCESS FOR 8-ARYLOCTANOIC ACIDS SUCH AS ALISKIREN

This application claims priority to U.S. Provisional Application Ser. No. 61/542,243 filled on Oct. 2, 2011.

BACKGROUND OF THE INVENTION

8-Aryloctanoic acids of a general formula I having the 2S,4S,5S,7S-configuration,

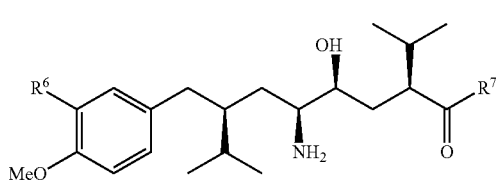

I especially compound such as Aliskiren, wherein $R^6$ represents $CH_3OCH_2CH_2CH_2O—$ and $R^7$—$NHCH_2C(CH_3)_2CONH_2$ (IUPAC name: 5-amino-N-(2-carbamoyl-2,2-dimethylethyl)-4-hydroxy-7-{[4-methoxy-3-(3-methoxypropoxy)phenyl]methyl}-8-methyl-2-(propan-2-yl)nonanamide), are excellent antihypertensive which interfere with the rennin-angiotensin system.

After discovery of the biological activity of the compound of formula I many syntheses, especially for Aliskiren, have been reported (U.S. Pat. No. 5,559,111 and EP 0 678 503). Since Aliskiren contains 4 chiral centers, synthesis of an enantiomerically pure compound is very complex. After 2001 many patents and publications have been published claiming various alternative routes to Aliskiren and the related compounds (WO 01/09083, WO 01/09079, EP 1 215 201, WO 02/02508, WO 02/02500, WO 02/02487, WO 02/08172, WO 02/092828, WO 02/02500, WO 03/103653, UK 2 431 640, GB 2 431 641, GB 2 431 642, GB 2 431 643, GB 2 431 644, GB 2 431 645, GB 2 431 646, GB 2 431 647, GB 2 431 48, GB 2 431 649, GB 2 431 650, GB 2 431 651, GB 2 431 652, GB 2 431 653, GB 2 431 654, WO 2005/054177, WO 2005/090305, WO 2005/051895, WO 2006/131304, WO2006/095020, WO2006/024501, WO2007/054254, WO2007/039183, EP 2 062 874, EP 1958 666, WO 2007/006532, WO2007/045420, WO2008/155338, WO2008/119804, CA 2 634 513, WO2007/048620, WO2007/118681, US2009/0076062, WO2010/010165, EP2189442, WO2009/049837, EP1958666, EP2189442, WO2009/049837, US2009/0076062, WO2011/082506, WO2011/019789, WO2011/064790, WO2010/112482, WO2010/010165, US2011/0092706, US2011/0105767, US2011/0137047, Tetrahedron Letters 2000, 41, 10085, ibid. 2000, 41, 10091, ibid. 2001, 42, 4819, Drugs Fut. 2001, 1139, J. Org. Chem. 2002, 67, 4261, Helv. Chim Acta 2003, 86, 2848, Tetrahedron Letters 2005, 46, 6337, J. Org. Chem. 2006, 71, 4766, Organic Process & Develop 2007, 11, 584, Tetrahedron Letters 2008, 49, 5980 and Org. Lett. 2010, 12, 1816). Nevertheless, none of them in the event fulfills necessary requirements for a cost effective manufacturing process on technical scale.

According to a concept filled in 1994 in the original U.S. Pat. No. 5,559,111, as well as later on in other patents (WO2007/045420), trans-configurated (2S,7S)-2,7-diisopropyloct-4-enedioic acid (or derivatives thereof) has been used as the starting material. C(5)-Amino and C(4)-hydroxy groups attached to this aliphatic $C_8$-chain have been introduced via three step reaction sequence, starting with halo lactonization of trans-double bond followed by displacement of the halogen with an azide and hydrogenation of the azide group. In an alternative approach recently published amino- and hydroxy-groups have been introduced more efficiently starting from cis-configurated (2S,7S)-2,7-diisopropyloct-4-enedioic acid by either direct nitro lactonization or aziridination of cis-double bond (US2011/0137047). Attachment of this chiral $C_8$-aliphatic fragment to the aromatic ring has been always accomplished via addition of an appropriate organometallic reagent, preferably Grignard reagent. The disadvantage of this approach is the use of an expensive trisubstituted aromatic compound such as 4-bromo-2-$R^6$ substituted anisole, which has been prepared from guajacol in 4 steps!, and which is required for the preparation of the organometallic reagent. As sufficiently documented in literature, preparation of organometallic reagents from aryl bromides containing electron-donating groups on the aromatic ring (as e.g. two alkoxy groups) is difficult and requires often special methods resulting in low overall yield. Consequently, synthesis of Aliskiren and related compounds is very expensive because the most expensive aliphatic $C_8$-building block with 4 chiral centers is not used efficiently.

On the other hand, alternative coupling of 2-substituted anisole of formula III with the chiral $C_8$-aliphatic building block of formula IV via Friedel-Crafts reaction has never been reported and such an approach represents a significant advantage against existing syntheses and it is now disclosed in the present invention.

SUMMARY OF THE INVENTION

The present invention discloses a novel efficient process for manufacture of enantiomerically pure compound of general formula V and I as shown in Scheme 1:

Scheme 1

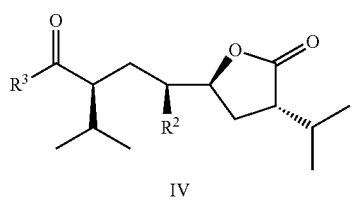

IV

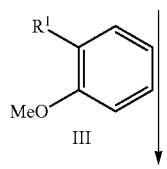

III

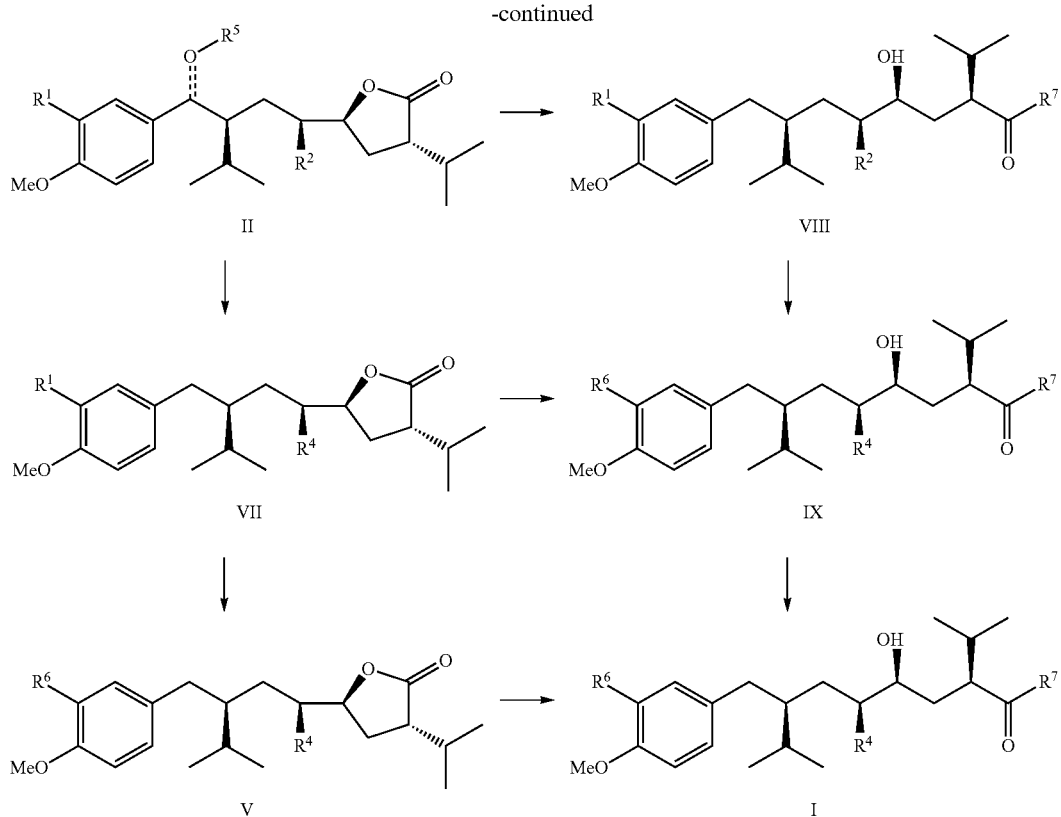

It has been unexpectedly found that the compound of formula V, a known intermediate in the synthesis of compound of formula I, can be prepared by a simple sequence of steps starting from a chiral compound of formula IV. The chiral compound of formula IV has been already prepared from cis- or trans-(2S,7S)-2,7-diisopropyloct-4-enedioic acid which had been obtained by double alkylation of 4(S)-benzyl-3-isovaleroyl-oxazolidin-2-one with either cis- or trans-1,4-dichloro-2-butene (U.S. Pat. No. 5,559,111 or US2011/0137047). As now disclosed this chiral compound of formula IV reacts under Friedel-Crafts condition with inexpensive, 2-$R^1$ substituted anisole of formula III providing in high yield a novel compound of formula II which can be reduced and, after exchange of $R^1$ group for $R^6$ group, easily converted into compound of formula V and then of formula I. Alternatively, the key compound of formula II can also be converted with $R^7$—H into an ester or amide of formula VIII. Subsequent reduction of $R^2$ group into $R^4$ group and final replacement of $R^1$ group with $R^6$ group provides also the compound of formula I.

DETAILED DESCRIPTION OF THE INVENTION

The present invention (Scheme 1) claims a process for preparation of a compound of formula V having the configuration as given in the formula,

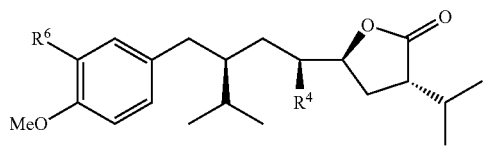

V wherein $R^6$ represents hydroxy, linear or brunched $C_{1-6}$ alkoxy, $C_{1-6}$ alkoxy-$C_{1-6}$-alkoxy, aryloxy, alkylaryloxy, arylalkoxy, preferably $CH_3OCH_2CH_2CH_2O$—, and $R^4$ represents $NHR^8$, wherein $R^8$ represents hydrogen, lower alkyl, aryl, alkylaryl, arylalkyl, preferably benzyl, mono-, di- or tri-methoxybenzyl, or other N-protective group, in particular one which together with N forms an amide or carbamate as —C(O)alkyl, —C(O)aryl, —C(O)alkylaryl, —C(O)arylalkyl, —C(O)Oalkyl, —C(O)Oaryl, —(O)COalkylaryl, —C(O)Oarylalkyl, preferably formyl, acetyl, trifluoroacetyl, —C(O)Obenzyl (Cbz) or —C(O)Otert.-butyl (BOC), comprising following steps:

a) reaction of a compound of formula IV,

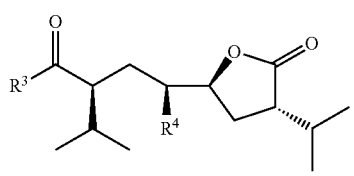

IV wherein $R^2$ represents —$NO_2$ or —$N_3$, or $NHR^8$, wherein $R^8$ is hydrogen, lower alkyl, aryl, alkylaryl, arylalkyl, preferably benzyl, mono-, di- or tri-methoxybenzyl, or other N-protective group, in particular one which together with N forms an amide or carbamate as —C(O)alkyl, —C(O)aryl, —C(O)alkylaryl, —C(O)arylalkyl, —C(O)Oalkyl, —C(O)Oaryl, —(O)COalkylaryl, —C(O)Oarylalkyl, preferably formyl, acetyl, trifluoroacetyl, —C(O)Obenzyl (Cbz) or —C(O)Otert.-butyl (BOC), and $R^3$ is hydrogen or halogen, preferably chlorine or bromine, or —OC(O)$R^9$ or —OC(O)O$R^9$, wherein $R^9$ is linear or brunched $C_{1-6}$-alkyl, preferably methyl or tert.-butyl, with a compound of formula III,

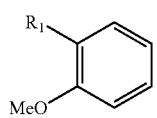

wherein $R^1$ represents halogen, preferably chlorine or bromine, alkanoyloxy, preferably formyloxy or trifluoracetoxy or acetoxy, FSO$_2$O— (fluorosulfonyloxy), an alkane-, arylalkane-, alkylarene-, arene-sulfonyloxy, preferably CH$_3$SO$_2$O— or Tosyloxy or CF$_3$SO$_2$O—, under Friedel-Crafts condition in the presence of a suitable catalyst used for Friedel-Crafts reaction such as bortrifluoroetherate, HN(SO$_2$CF$_3$)$_2$, metal salt, preferably Al-, Ti-, Zn-, Zr-, Bi-, lanthanide-halide or triflate, providing compound of formula II,

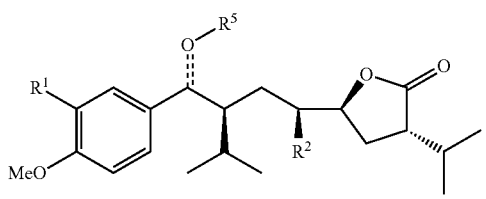

wherein $R^1$ is the same as defined in compound of formula III,
$R^2$ is as defined in compound of formula IV,
$R^5$ is either void when the dotted lines are a double bond representing carbonyl, or $R^5$ is hydrogen when the dotted lines are representing one single bond as a sec.-alcohol;

b) reduction of oxo- or hydroxy-group at C(8)-atom and N$_3$- or NO$_2$-group at C(5)-atom, when $R^2$ is N$_3$- or NO$_2$-group as defined in the compound of formula II, in one or more separate steps, with a reducing agent containing either a hydride as reducing agent, preferably metal hydrides or silanes, or by homogeneous or heterogeneous hydrogenation in the presence of transition metal, preferably such as Ra—Ni, Pd, Pt or Rh,
followed by removal of $R^1$-group and replacing it by $R^6$-group as defined for the compound of formula V, accomplished in one or in a few separate steps, by
i) either direct substitution of $R^1$ group with nucleophilic reagent $R^6$—H containing $R^6$ group such as hydroxy, alkoxy, alkylaryloxy, arylalkoxy, preferably CH$_3$OCH$_2$CH$_2$CH$_2$O—, without or in the presence of a catalyst such as metal or salt thereof, preferably transition metal or salt thereof such as Cu or Pd or salt thereof,
ii) or alternatively by selective cleavage of $R^1$ group, when $R^1$ is alkanoyloxy such as acetoxy, formyloxy, trifluoracetoxy, or FSO$_2$O-(fluorosulfonyloxy), an alkane-, arylalkane-, alkylarene-, arene-sulfonyloxy, preferably CH$_3$SO$_2$O—, Tosyloxy and CF$_3$SO$_2$O—, under basic or acidic or reductive condition, forming initially phenol followed by alkylation thereof with a suitable alkylation reagent $R^6$-Lvg, wherein Lvg is a leaving group and $R^6$ is as defined for $R^6$ group, preferably by alkylation of phenolic group, or an alkali metal salt thereof such as phenolate, with CH$_3$OCH$_2$CH$_2$CH$_2$—X, wherein X is chlorine or bromine,
or vice versa by first removal of $R^1$-group and replacing it by $R^6$-group followed by reduction of oxo- or hydroxy-group at C(8)-atom and alternatively N$_3$- or NO$_2$-group at C(5)-atom.

The chiral compound of formula IV can be prepared from either cis- or trans-(2S,7S)-2,7-diisopropyloct-4-enedioic acid via either nitro lactonization or aziridination of cis-double bond or via bromo lactonization of trans-double bond followed by displacement of halogen with an azide (U.S. Pat. No. 5,559,111 or US2011/0137047). This compound of formula IV can be reacted with compound of formula III under Friedel-Crafts conditions as known to a person skilled in the art in the presence of catalyst commonly used for Friedel-Crafts reaction such as bortrifluoroetherate, HN(SO$_2$CF$_3$)$_2$, any metal salt, preferably Al-, Ti-, Zn-, Zr-, lanthanide-, Hf-, Bi-halide or triflate (as reported e.g. in Tetrahedron Letters 2003, 44, 2937, ibid. 2003, 44, 5343, Tetrahedron 2004, 60, 10843, ibid. 1995, 36, 409, ibid. 2002, 43, 6331, Tetrahedron 2006, 62, 9201, Bioorg. Med. Chem. 2010, 18, 971). As solvent aprotic organic solvent, preferably chlorinated hydrocarbons as methylenechloride, dichloroethane, or aliphatic hydrocarbons, preferably hexane or heptane, or in the presence of some catalysts even aromatic hydrocarbons as toluene can be used at temperature between −78 C until reflux, preferably at rt.

In the preferred embodiment of the invention in the compound of formula III (2-substituted anisole) $R^1$ group is either halogen, preferably chlorine or bromine, or oxygen substituted with an electron withdrawing group such as FSO$_2$O—, an alkane-, arylalkane-, alkylarene-, arene-sulfonyloxy, preferably —OMs, —OTs or —OSO$_2$CF$_3$. Either halogen or any of these electron withdrawing groups deactivate specifically the corresponding 5-position on the aromatic ring compare to electron-rich methoxy group which selectively activates 4-position allowing thus, regioselective Friedel-Crafts reaction at this position in high yield.

Reduction of 8-oxo or 8-hydroxy group and 5-nitro or 5-azido groups in the compound of formula II (Scheme 2b) can be achieved either simultaneously or in a few separate steps using either chemical reducing agent containing hydride as e.g. silane, preferably triethylsilane or tetramethyl disiloxane (TMDS) or polymeric siloxane (PMHS) in the presence of acid as trifluoroacetic or triflic acid, or various Lewis acids as aluminum or titanium chloride, or alkali or earth alkali metal hydride as LiBH$_4$, NaBH$_4$ itself or in the presence of PTC-catalyst or transition metal salt such as Cu-, Ti- or Zr-halides, or even using hydrogen as heterogeneous or homogenous or transfer hydrogenation in the presence of transition metal such as Pt, Pd, Ra—Ni, Rh etc.

The preferred reduction method for 8-oxo or 8-hydroxy group is reduction with silanes in the presence of acid, preferably triethylsilane in the presence of triflic or trifluoroacetic acid or Lewis acid as bortrifluoroetherate, ZnCl$_2$, AlCl$_3$ or TiCl$_4$, or tetramethyl disiloxane (TMDS) or polymeric siloxane (PMHS) in the presence of Lewis acid, preferably such as aluminum or titanium chloride, at reaction temperature between −78 C until reflux, preferably at rt.

Since the reaction conditions for reduction of 8-oxo or 8-hydroxy group with silanes in the presence of Lewis acids are very similar to conditions used for Friedel-Crafts reaction, both step can be perform in situ in one reaction vessel as shown in Experimental section. Preferably Friedel-Crafts reaction between compounds of formula III and the compound of formula IV can be carried out in methylenechloride in the presence of aluminum or titanium chloride and after completion of Friedel-Crafts reaction the reducing agent TMDS or triethylsilane can be added to accomplish reduction of 8-oxo or 8-hydroxy function (s. e.g. Heterocycles 1998, 49, 233 or Organic Process Research & Development 2008, 12, 1142) providing in one operation step directly the compound of formula VI (Scheme 2b).

In some cases in compound of formula II, wherein $R^1$ is an alkane-, arylalkane-, alkylarene-, arene-sulfonyloxy group, homogeneous or heterogeneous hydrogenation in the presence of common hydrogenation catalyst as know to a person skilled in the art, preferably Pt—C or Pd—C or $R^h$, can be used. Accordingly, compound of formula II can be then reduced directly to a compound of formula VII because oxo- or hydroxy-group at C(8)-atom as well as $N_3$- or $NO_2$-group at C(5)-atom, when $R^2$ is $N_3$- or $NO_2$-group, are reduced simultaneously in one hydrogenation step.

In compound of formulas II and VI, wherein $R^1$ is halogen and $R^2$ is either $N_3$- or $NO_2$-group, $N_3$- or $NO_2$-groups are preferably reduced under other conditions than catalytic hydrogenation. For reduction of $NO_2$-group sodium borohydride in the presence of zirconium chloride in THF can be used as reported in Syntlett 2000, 5, 683. For reduction of azido group preferably copper sulfate and sodium borohydride (Synthetic Commun. 1994, 24, 549) or 1,3-dithiopropane (Tetrahedron Letters 1978, 39, 3633) or trimethylsilyl iodide (Tetrahedron Letters 1997, 38, 6945) can be used.

In the compound of formulas II and IV, wherein $R^2$ is $NNR^8$, wherein $R^8$ is hydrogen, lower alkyl, aryl, alkylaryl, arylalkyl, preferably benzyl, mono-, di- or tri-methoxybenzyl, or other N-protective group, in particular one which together with N forms an amide or carbamate as —C(O)alkyl, —C(O)aryl, —C(O)alkylaryl, —C(O)arylalkyl, —C(O)Oalkyl, —C(O)Oaryl, —(O)COalkylaryl, —C(O)Oarylalkyl, preferably —$NH_2$.HCl (ammonium hydrochloride salt), formyl, acetyl, trifluoroacetyl, —C(O)Obenzyl (Cbz), —C(O)Otert.-butyl (BOC), preferably $R^2$ is, the reduction step includes only reduction of 8-oxo- or 8-hydroxy groups at C(8)-atom by anyone of methods discussed above for this step, preferably in situ after Friedel-Crafts reaction with triethylsilane or tetramethyl disiloxane in the presence of aluminum or titanium chloride at reaction temperature 0° C. to rt.

After reduction step in the compound of formula VII (Scheme 2b) protecting group $R^1$ is removed and replaced with $R^6$ group as defined for the compound of formula V: The removal of $R^1$ group and replacing it by $R^6$ group can be carried out in one or a few separate steps, by either direct substitution of $R^1$ group with a nucleophilic reagent $R^6$—H containing $R^6$ group such as hydroxy, alkoxy, alkylaryloxy, arylalkoxy, preferably $CH_3OCH_2CH_2CH_2O$—, without or in the presence of a catalyst such as metal or salt thereof, preferably transition metal or salts thereof such as Cu or Pd or salts and complexes thereof.

In the preferred embodiment of the invention $R^1$ is halogen, preferably bromine, which can be directly substituted with alkali or earth alkali hydroxide or alcoholate, preferably alcoholate derived from $CH_3OCH_2CH_2CH_2OH$, such as $CH_3OCH_2CH_2CH_2O^-Na^+$, in the presence of a transition metal, preferably Cu(I) or Cu(II)-salt or Pd(0)- or Pd(II)-salt in the presence of chelating agent(s), providing the compound of formula V (s. conditions as reported in J. Chem. Soc. Chem. Commun. 1993, 419, J. Org. Chem. 2009, 74, 5075, J. Am. Chem. Soc. 2010, 132, 11592).

Alternatively, in the compound of formula VII, wherein $R^1$ is alkanoyloxy- such as acetoxy, formyloxy, trifluoracetoxy, or alkane-, arylalkane-, alkylarene-, arene-sulfonyloxy group such as $CH_3SO_2O$—, Tosyloxy-, $CF_3SO_2O$—, or $FSO_2O$—, the cleavage of $R^1$ group can be carried out under basic or acidic or reductive condition as known to a person skilled in the art providing compound of formula V, wherein $R^6$ is phenolic hydroxy group, which can be then selectively alkylated with suitable alkylation reagent chosen according to definition of $R^6$-group, preferably, alkylation of phenol or an alkali or earth alkali phenolate, with a suitable alkylating agent defined as $R^6$-Lvg, wherein Lvg is a common leaving group as known to a person skilled in the art, preferably $CH_3OCH_2CH_2CH_2$—X, wherein X is chlorine or bromine, providing the compound of formula V (Tetrahedron Letters 2002, 43, 4281).

As further embodiment of the invention in vice versa approach (Scheme 2a), the compound of formula II can be first converted into a compound of formula X by replacing $R^1$-group with $R^6$-group by any method as discussed above, followed then by reduction of oxo- or hydroxy-group at C(8)-atom and $N_3$- or $NO_2$-group at C(5)-atom leading to compound of formula V.

Scheme 2a

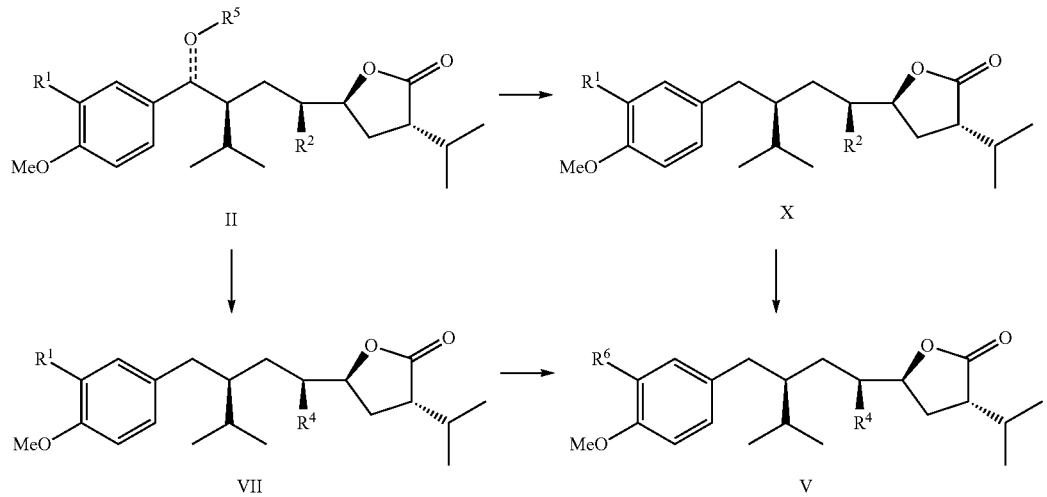

Final conversion of the compound of formula V into the compound of formula I is already sufficiently reported in literature (Scheme 2b):

Reaction of compound of formula V with compound $R^7$—H, preferably $NH_2CH_2C(CH_3)_2CONH_2$, can be carried out in two different ways;

i) Comprising either initial opening of 5-membered lactone ring, protection of 4-hydroxy group and reaction of free carboxylic acid, or ester thereof, with $R^7$—H by a method known a person skilled in the art for preparation of ester or amides ii) or alternatively by direct reaction of the lactone of formula V with $R^7$—H as reported in Novartis patent (p. 22, 23, 24, 31, 32 in U.S. Pat. No. 5,559,111). Preferably lactone of formula V can be reacted directly with $NH_2CH_2C(CH_3)_2CONH_2$ as reported in EP-A-678 503 (p. 124, 130 and 131) or WO02/02508 (example H1 p. 35, preparation of J1) or U.S. Pat. No. 5,559,111 (example 83).

As a further embodiment of the invention the compound of formula VI can be reacted with $R^7$—H, similar as discussed above for conversion of compound of formula V into the final compound of formula I (Scheme 2b), providing compound of formula VIII. Subsequent replacement of $R^1$-group with $R^6$-group and reduction of $R^2$-group into $R^4$-group can be carried out in the same way as already described above.

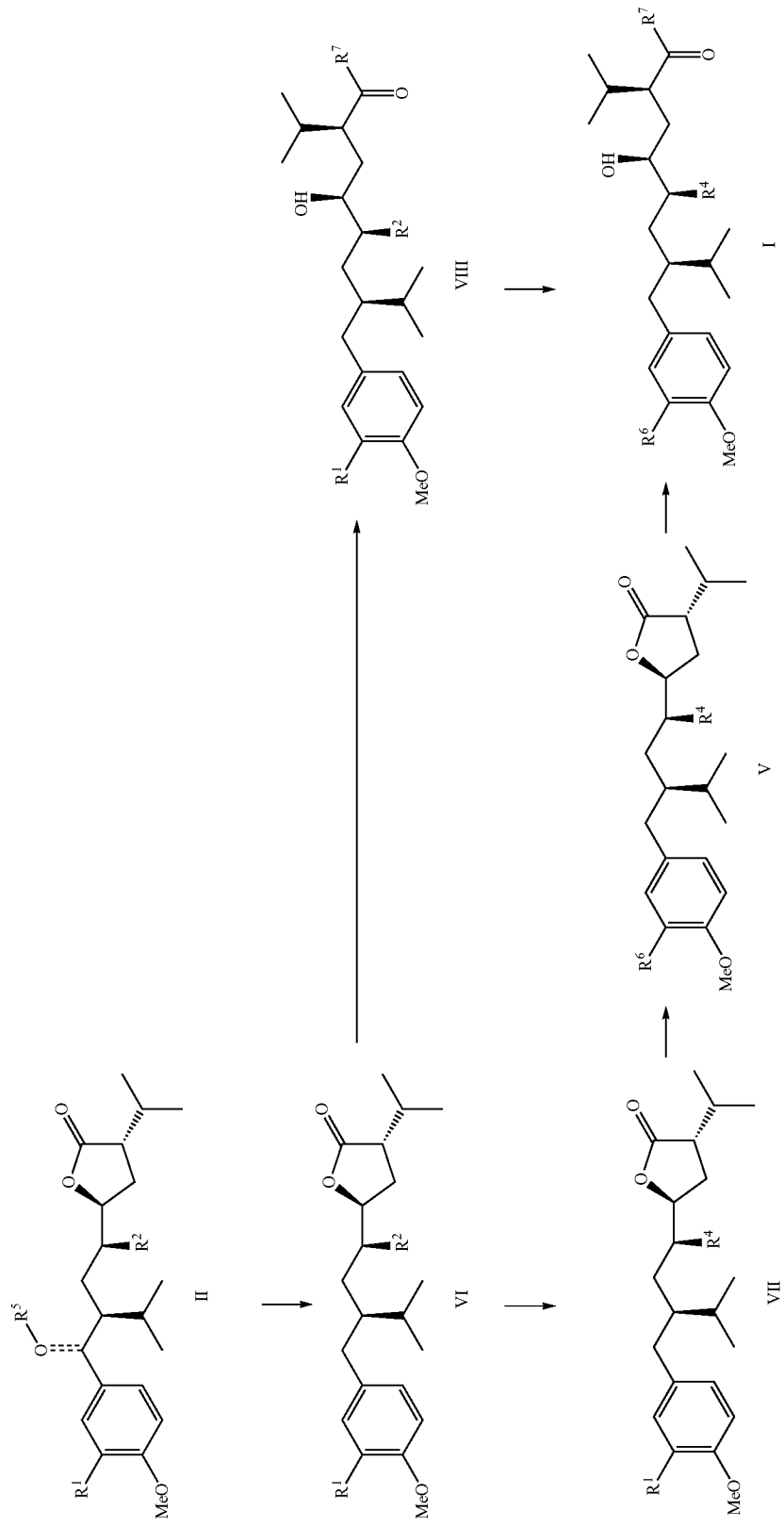

As a further embodiment of the invention depending on the number of asymmetric carbon atoms in the molecule and on choice of starting materials, all compounds can be present in the form of as enantiomerically pure compound or as racemate of one possible isomer or as a mixture of stereoisomers or mixture of racemates. The invented process for enantiomerically pure compound of formulas II, IV, V, VI and VII as shown in Schemes 1 and 2 can be applied also for preparation of racemic compound which can be subjected at any stage of the synthesis to a resolution or separation step using (chiral) agent or including an enzymatic step or another separation method known as preparative HPLC or SMB etc.

In a further embodiment of the invention the compound of formula V,

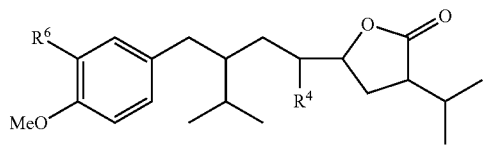

V wherein $R^6$ represents linear or brunched $C_{1-6}$ alkoxy, $C_{1-6}$ alkoxy-$C_{1-6}$-alkoxy, aryloxy, alkylaryloxy, arylalkoxy, preferably $CH_3OCH_2CH_2CH_2O$—, and
$R^4$ represents hydroxy or lower alkanoyloxy or an alkane-sulfonyloxy-, preferably $CH_3SO_2O$—, $CF_3SO_2O$—, or halogen, preferably chlorine, bromine, or $NHR^8$, wherein $R^8$ is hydrogen, alkyl, aryl, alkylaryl, arylalkyl, preferably —$NH_2$, benzyl, mono-, di- or tri-methoxybenzyl, or other N-protective group, in particular one which together with N forms an amide or carbamate as —C(O)alkyl, —C(O)aryl, —C(O)alkylaryl, —C(O)arylalkyl, —C(O)Oalkyl, —C(O)Oaryl, —(O)COalkylaryl, —C(O)Oarylalkyl, preferably formyl, acetyl, trifluoroacetyl, —C(O)Obenzyl (Cbz), —C(O)Otert.-butyl (BOC),
can be prepared by
a) Friedel-Crafts reaction of the compound of formula IV,

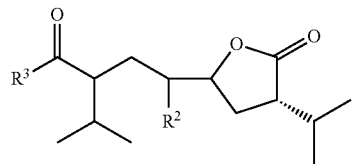

IV wherein $R^2$ represents —$NO_2$ or —$N_3$, or hydroxy or lower alkanoyloxy or an alkane-sulfonyloxy-, preferably $CH_3SO_2O$—, $CF_3SO_2O$—, or halogen, preferably chlorine, bromine, or $NHR^8$, wherein $R^8$ is hydrogen, alkyl, aryl, alkylaryl, arylalkyl, preferably —$NH_2$, benzyl, mono-, di- or tri-methoxybenzyl, or other N-protective group, in particular one which together with N forms an amide or carbamate as —C(O)alkyl, —C(O)aryl, —C(O)alkylaryl, —C(O)arylalkyl, —C(O)Oalkyl, —C(O)Oaryl, —(O)COalkylaryl, —C(O)Oarylalkyl, preferably formyl, acetyl, trifluoroacetyl, —C(O)Obenzyl (Cbz), —C(O)Otert.-butyl (BOC), and
$R^3$ is hydrogen or hydroxy or halogen, preferably chlorine or bromine, or —$OC(O)R^9$ or —$OC(O)OR^9$, wherein $R^9$ is linear or brunched $C_{1-6}$-alkyl, preferably methyl and ethyl,
with a compound of formula III,

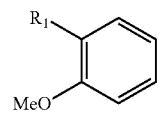

III wherein $R^1$ represents halogen, preferably chlorine or bromine, alkanoyloxy, preferably acetoxy or formyloxy or trifluoracetoxy, an alkane-, arylalkane-, alkylarene-, arene-sulfonyloxy, preferably $CH_3SO_2O$— or Tosyloxy or $CF_3SO_2O$—,
providing a compound of formula II,

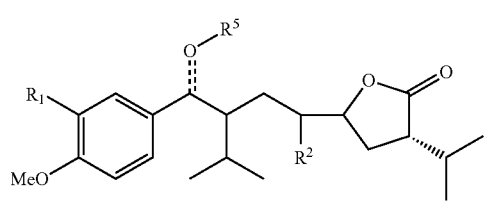

II wherein $R^1$ is the same as defined in compound of formula III,
$R^2$ is as defined in compound of formula IV,
$R^5$ is either void when the dotted lines are a double bond representing carbonyl,
or $R^5$ is hydrogen when the dotted lines are representing one single bond as sec.-alcohol;
b) followed by reduction of oxo- or hydroxy-group at C(8)-atom and alternatively $N_3$- or $NO_2$-group at C(5)-atom, when $R^2$ is either —$NO_2$ or —$N_3$, in one or in a few separate steps, with a suitable reducing agent as discussed above, followed
by removal of $R^1$-group and replacing it by $R^6$-group as defined in the compound of formula V, in one or more separate steps, by one of the methods as disclosed above, or vice versa by first removal of $R^1$-group and replacing it by $R^6$-group followed by reduction of oxo- or hydroxy-group at C(8)-atom and alternatively $N_3$- or $NO_2$-group at C(5)-atom.

In this invention a characteristic of protective groups is that they can be removed readily (without the occurrence of undesired secondary reactions) for example by solvolysis, reduction, or alternatively under physiological conditions (as e.g. enzymatic cleavage or formation). Different protective groups can be selected so that they can be removed selectively at different stages of the synthesis while other protective groups remain intact. The corresponding alternatives can be selected readily by a person skilled in the art from those given in the standard reference works mentioned in literature (as e.g. Mc Omie "Protective Groups in Organic Chemistry" or Green et al. "Protective Groups in Organic Synthesis") or in the description or in the claims or the Examples.

When referring to compounds described in the present invention, it is understood that references are also being made to salts thereof.

The examples are provided to illustrate particular aspects of the disclosure and do not limit the scope of the present invention as defined by the claims.

EXAMPLES

Determination of optical purity was carried out with HPLC using chiral columns as Chiralcel OJ-H, Chiralpak AS-H or Chiralpak AD-H from Daicel Chem. Ind. In some cases the optical purity was also determined with NMR-Spectroscopy using chiral Eu-shift reagent. If not mentioned otherwise, all evaporations are performed under reduced pressure, preferably between 5-50 Torr in some case even under high vacuum (0.05 Torr). The structure of final products, intermediates and starting materials has been confirmed by standard analytical methods, e.g. spectroscopic characteristics as MS or NMR or IR. Abbreviation used are those conventional in the art.

Preparation of 3(S)-isopropyl-5(S)-{1(S)—BOC-amino-3(S)-isopropyl-4-[4-methoxy-3-(3-methoxypropyloxy)-phenyl]-butyl}-tetrahydrofuran-2-one (Va) from 3(S)-isopropyl-5(S)-[1(S)-azido-3(S)-isopropyl-4-chloro-4-oxobutyl]-tetrahydrofuran-2-one (IVa) as shown in Scheme 3 was heated to 40° C. for ca. 1 hr until acid chloride IVa was fully consumed. The reaction was monitored by TLC and HPLC. After completion crude reaction mixture was poured very slowly on ice (3 kg), the organic phase separated, the aqueous phase filtered and then extracted 3 times with methylenechloride (3×500 ml). The combined organic phases were washed once with water (300 ml), once with sat.-NaHCO$_3$-solution (400 ml), then with brine (400 ml) and dried over sodium sulfate, filtered and the filtrate concentrated under reduced pressure. The excess of 2-bromoanisole was removed by high vacuum distillation (0.05 Torr) at ca. 80-100° C. The residue was dissolved in methylenechloride (700 ml), treated with charcoal (50 g), the solution stirred for ca. 20 min, then filtered and the filtrate concentrated under reduced pressure providing a yellow semi-crystalline IIa (430 g, 92% yield resp. to IVa). This material was directly used for the next step (IIa→VIIa):

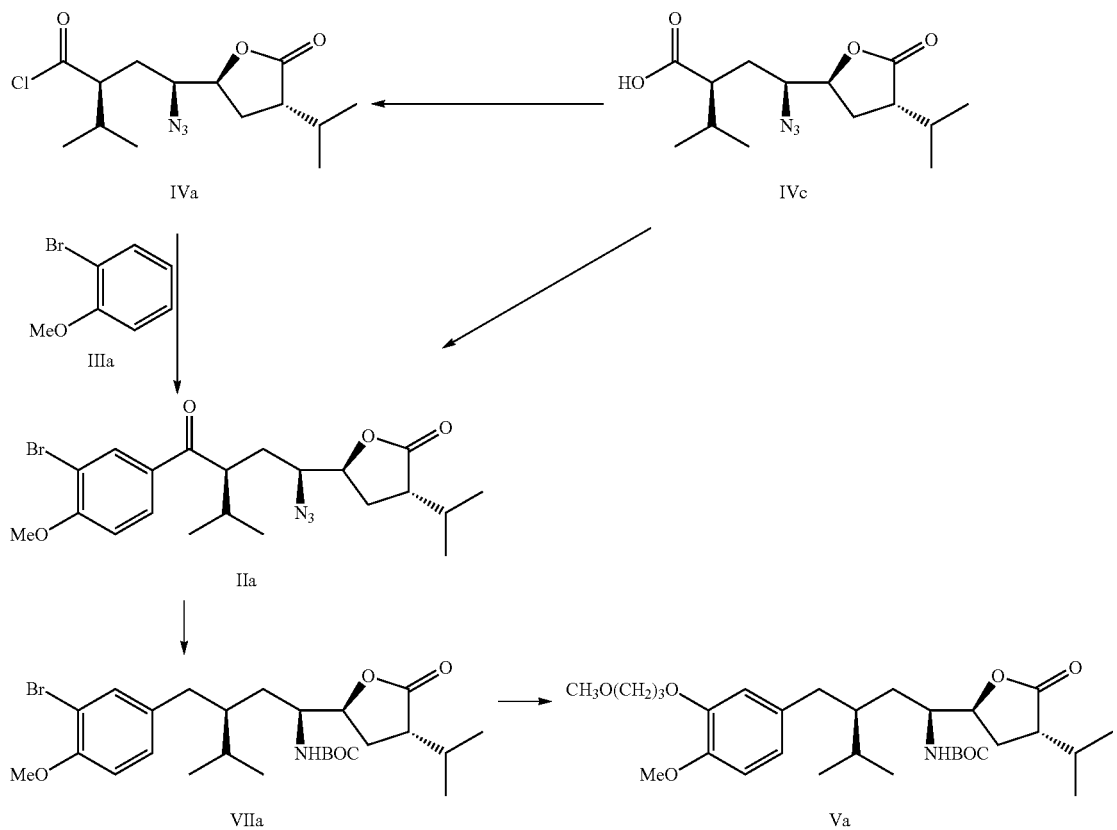

Scheme 3

Example 1

Preparation of IIa from IVa and IIIa

Under inert atmosphere to a stirred solution of 2-bromoanisole (300 g) in methylenechloride (1000 ml), AlCl$_3$ (320 g) was slowly added at rt. To the resulting slurry acid chloride IVa (315 g, prepared from the corresponding acid IVc as reported in U.S. Pat. No. 5,559,111 on page 30 and 80 in example 81l or in EP2189442 example 18), dissolved in methylenechloride (600 ml), was slowly added that the reaction temperature remained below 30° C. (ice cooling!). After stirring at that temperature for 45 min the reaction mixture For analytical purposes a small sample of crude IIa was purified by recrystallization from toluene/hexane: Anal. calculated for $C_{21}H_{28}BrN_3O_4$: C, 54.08; H, 6.05; Br, 17.13; N, 9.01; O, 13.72. Found: C, 5413; H, 6.18; Br, 16.99; N, 9.06; O, 13.80.

Example 2

Preparation of IIa from IVc and IIIa

Under inert atmosphere a mixture of HNTf2 (5 g), 2-bromoanisole (350 g), the acid IVc (30 g, prepared as reported in U.S. Pat. No. 5,559,111 on page 30 and 80 in example 81k) in toluene (400 ml) was refluxed for 36 hrs in 2 l flask equipped with Dean-Stark apparatus until acid IVc was fully consumed. The reaction was monitored by TLC and HPLC. After completion and cooling to rt the reaction mixture was poured on ice (500 g), the organic phase separated, the aqueous phase filtered and then extracted 3 times with ethyl acetate (3×100 ml). The combined organic phases were washed once with water (100 ml), once with sat.-NaHCO$_3$-solution (50 ml), then with brine (50 ml) and dried over sodium sulfate, filtered and the filtrate concentrated under reduced pressure. The excess of 2-bromoanisole was removed by distillation on high vacuum (0.05 Torr) at ca. 80-100° C. The residue was dissolved in ethylacetate (100 ml), treated with charcoal (2 g), the solution stirred for ca. 20 min, then filtered and the filtrate concentrated under reduced pressure providing crystalline IIa (39 g, 84% yield). This material was directly used for the next step (IIa→VIIa): For analytical purposes a small sample of the crude IIa was purified by recrystallization from toluene/hexane.

Example 3

Preparation of VIIa from IVa and IIIa

Under inert atmosphere to a stirred solution of 2-bromoanisole (300 g) in methylenechloride (1500 ml) AlCl$_3$ (270 g) was slowly added at 10-15° C. To the resulting slurry acid chloride IVa (315 g, prepared from the corresponding acid IVc as reported in U.S. Pat. No. 5,559,111 on pages 30 and 80 in example 811), dissolved in methylenechloride (200 ml), was slowly added over 2 hrs that the reaction temperature remained between 30-40° C. (ice cooling!). After addition the reaction mixture was heated to 35-40° C. for ca. 1-2 hrs until acid chloride IVa was fully consumed. The reaction was monitored by TLC and HPLC. After completion the reaction mixture was cooled to 0-5° C., 1,1,3,3-tetramethyldisiloxane (270 g) was slowly added and the mixture stirred at this temperature for 4-6 hrs. After completion of the reduction (monitored by TLC and HPLC) the mixture was poured very slowly on ice water (3 kg). The HCl gas that evolved during this quench was scrubbed by a caustic scrubber. The organic phase was separated and the aqueous phase filtered, extracted 3 times with methylenechloride (3×500 ml). The combined organic phases were washed once with water (300 ml), once with sat.-NaHCO$_3$-solution (400 ml), finally with brine (400 ml), dried over sodium sulfate, filtered and the filtrate concentrated under reduced pressure. Excess of 2-bromoanisole was removed by distillation on high vacuum (0.05 Torr) at ca. 80-100° C., the residue then dissolved in methylenechloride (400 ml), treated with charcoal (10 g), the solution stirred for ca. 20 min, filtered and the filtrate concentrated under reduced pressure providing yellow crystalline intermediate, 3(S)-isopropyl-5(S)-{1(S)-azido-3(S)-isopropyl-4-[4-methoxy-3-bromo-phenyl]-butyl}-tetrahydrofuran-2-one: 395 g (87% yield resp. to IVa). This material was directly used for the reductive step as shown in anyone of the following examples a-c):

a) Under inert atmosphere to a solution of crude 3(S)-isopropyl-5(S)-{1(S)-azido-3(S)-isopropyl-4-[4-methoxy-3-bromo-phenyl]-butyl}-tetrahydrofuran-2-one (45 g from the above Example 3) in dry acetonitrile (300 ml) sodium iodide (23 g) was added and the mixture stirred at rt for ca. 30 min. To this stirred solution TMS-Cl (16.5 g) in acetonitrile (30 ml) was added dropwise and the stirring continued for 20-60 min until the reaction was completed. The reaction conversion was monitored by HPLC and TLC. For work up the reaction mixture was quenched with 10% sodium thiosufate solution (100 ml), the product extracted from the aqueous phase 3 times with ethyl acetate (3×200 ml), the combined organic phases washed twice with brine (2×200 ml), dried with sodium sulfate (150 g), filtered, the filtrate concentrated under reduced pressure to ca. 200 ml volume. To this solution N,N-dimethylaminopyride (0.2 g), triethylamine (11 g) and di-tert-butyldicarbonate (35 g) were added at rt and the mixture stirred for 24 hrs to achieve complete BOC-protection of the amino group. After careful acidification of the reaction mixture with glacial acetic acid, the mixture was extracted with toluene/water mixture and the organic phase separated, dried and evaporated under reduced pressure providing oily VIIa: 45.1 g (86% yield)

b) Under inert atmosphere to a cooled (0-5° C.) and stirred mixture of copper sulphate pentahydrate (0.50 g) in methanol (100 ml) NaBH$_4$ (1.5 g) was added. To the resulting black suspension at 0-5° C. crude 3(S)-isopropyl-5(S)-{1(S)-azido-3(S)-isopropyl-4-[4-methoxy-3-bromo-phenyl]-butyl}-tetrahydrofuran-2-one (45 g, prepared in the above Example 3) in dry methanol (200 ml) was then slowly added. Reaction was continued by further addition of NaBH$_4$ (3 g) in four portions during 1-2 hrs and the stirring continued until the reaction was completed. The reaction conversion was monitored by HPLC and TLC. The reaction mixture was filtered through celite, to the filtrate glacial acetic acid (ca. 50 ml) was added, the solvents concentrated under reduced pressure to a volume of ca. 200 ml, then N,N-dimethylaminopyride (0.4 g), triethylamine (15 ml) and finally di-tert-butyldicarbonate (36 g) were added at rt and the mixture stirred for 24 hrs to achieve complete BOC-protection of amino group. After careful acidification of the reaction mixture with glacial acetic acid, the mixture was poured on water (500 ml), and the aqueous phase extracted with 3 times with ethylacetate (3×200 ml), the organic phase separated and evaporated under reduced pressure. The residue was dissolved in acetic acid (100 ml), the solution stirred for 1 hr at 35° C. until lactone formation was completed (monitored by TLC and HPLC), then acetic acid was removed under reduced pressure providing crude VIIa as crystalline material: 48.1 g (91% yield). For analytical purposes a small sample of the crude VIIa from Experiments a) or b) was purified by recrystallization from ethylacetate/hexane: Anal. calculated for C$_{26}$H$_{40}$BrNO$_5$: C, 59.31; H, 7.66; Br, 15.18; N, 2.66; O, 15.9. Found: C, 59.35; H, 7.70; Br, 15.08; N, 2.60; O, 15.25.

c) Under inert atmosphere 3(S)-isopropyl-5(S)-{1(S)-azido-3(S)-isopropyl-4-[4-methoxy-3-bromo-phenyl]-butyl}-tetrahydrofuran-2-one (45 g, prepared in the above Example 3) was dissolved in freshly distilled methanol (500 ml) at rt. To this stirred solution propane-1,3-dithiol (30 g) and dry triethylamine (30 g) were added and the solution stirred at rt until the reaction was completed (ca. 2 days). The reaction conversion was monitored by HPLC and TLC. For the work up reaction mixture was evaporated under reduced pressure to dryness, the residue dissolved in aqueous conc.-HCl (1:1, ca. 200 ml), the solution stirred for ca. 1 hr at rt, and the hydrochloride salt then extracted from the aqueous phase 3 times with methylenechloride (3×200 ml), the combined organic phases washed once with brine (100 ml), dried with sodium sulfate (150 g), filtered, the filtrate concentrated under reduced pressure providing crude 3(S)-isopropyl-5(S)-{1(S)-amino-3(S)-isopropyl-4-[4-methoxy-3-bromo-phenyl]-butyl}-tetrahydro-furan-2-one hydrochloride: 42 g (93% yield).

Example 4

Preparation of VIIa from IIa

Under inert atmosphere crude IIa (47 g, prepared in Example 1 or 2) was dissolved in methylenechloride (500 ml) and triethylsilane (36 g) was added at 0° C. To this solution under stirring at 0° C. TiCl$_4$ (60 g) was slowly added that the reaction temperature was maintained at 0° C. After being stirred at rt for ca. 15 hrs the reaction was completed (monitored by TLC and HPLC). The mixture was poured slowly on ice (500 g) the organic phase separated, the aqueous phase filtered and then extracted 3 times with methylenechloride (3×100 ml). The combined organic phases were washed once with water (100 ml), once with sat.-NaHCO$_3$-solution (100 ml), then with brine (100 ml) and dried over sodium sulfate, filtered and the filtrate concentrated under reduced pressure. The residue was dissolved in methylenechloride (400 ml), treated with charcoal (5 g), the solution stirred for ca. 20 min, then filtered and the filtrate concentrated in vacuum providing semi-crystalline intermediate, 3(S)-isopropyl-5(S)-{1(S)-azido-3(S)-isopropyl-4-[4-methoxy-3-bromo-phenyl]-butyl}-tetrahydrofuran-2-one: 39.5 g (87% yield). This material was directly used for the reductive step as shown in Example 3 Section a) or b providing VIIa.

Example 5

Preparation of Va from VIIa

In autoclave 3-methoxy-1-propanol (300 ml) was loaded and under inert atmosphere sodium hydride (10 g), was slowly added to form the corresponding alcoholate (hydrogen evolution!). To this solution crude VIIa (53 g, prepared in Examples 3 or 4) and dry carbon dioxide (1.5 g) were added, the autoclave closed and the reaction mixture heated at 100-110° C. for 3 hrs. The reaction was completed when VIIa, as well as a lactone opening intermediate (3-methoxy-1-propyl ester of VIIa), were both consumed (monitored by TLC and HPLC after a sample was first treated with 30% aq. sodium hydroxide, extracted with ethylacetate and then acidified with acetic acid). For work up the mixture was poured on 30%-aqueous NaOH-solution (50 ml), stirred at rt for ca. 2 hrs, then acidified carefully with cold conc.-37% HCl to pH 4-5! and the aqueous phase extracted 3 times with ethylacetate (3×200 ml). The combined organic phases were washed once with brine (100 ml), dried over sodium sulfate, filtered and the filtrate concentrated under reduced pressure. The residue was dissolved in acetic acid (100 ml), the solution stirred for 1 hr at 30-35° C. until lactone formation was completed (monitored by TLC and HPLC), then filtered and the filtrate concentrated under reduced pressure providing an oil as Va: 40 g (75% yield).

The analytical data of Va were identical as reported in e.g. WO2006/024501 on page 58 as Example K) or WO2008/119804 on page 67 as Example 18. or in US2009/0076062 Example 26b) and c).

Example 6

Preparation of Va from VIIa

Under inert atmosphere (argon) to 3-methoxy-1-propanol (300 ml) CuI (1 g), 8-hydroxyquinoline (7 g), K$_3$PO$_4$ (43 g) and crude VIIa (53 g, prepared in Examples 3 or 4) were added, the apparatus 3 times evacuated and refilled with argon. The reaction mixture was heated under stirring at 110° C. for 40 hrs. The reaction was completed when VIIa, as well as a lactone opening intermediate (3-methoxy-1-propyl ester of VIIa), were both consumed (monitored by TLC and HPLC after a sample was first treated with 30% aq. sodium hydroxide, extracted with ethylacetate and then acidified with acetic acid). For work up the mixture was poured on water (1000 ml) and the aqueous phase extracted 3 times with toluene (3×300 ml). The combined organic phases were washed twice with brine (2×200 ml), dried over sodium sulfate, filtered and the filtrate concentrated under reduced pressure. The residue was dissolved in acetic acid (200 ml), the solution stirred for 1 hr at 35-40° C. until lactone formation was completed (monitored by TLC and HPLC), then charcoal (2 g) was added, the suspension filtered and the filtrate concentrated in vacuum providing brownish crystalline Va: 35 g (65% yield). The analytical data of Va (after purification of a small sample) were identical as reported in e.g. WO2006/024501 on page 58 as Example K) or WO2008/119804 on page 67 as Example 18. or in US2009/0076062 Example 26b) and c).

Preparation of 3(S)-isopropyl-5(S)-{1(S)—BOC-amino-3(S)-isopropyl-4-[4-methoxy-3-(3-methoxypropyloxy)-phenyl]-butyl}-tetrahydrofuran-2-one (Va) from 3(S)-isopropyl-5(S)-[1(S)-nitro-3(S)-isopropyl-4-chloro-4-oxobutyl]-tetrahydrofuran-2-one (IVb) as shown in Scheme 4

Scheme 4

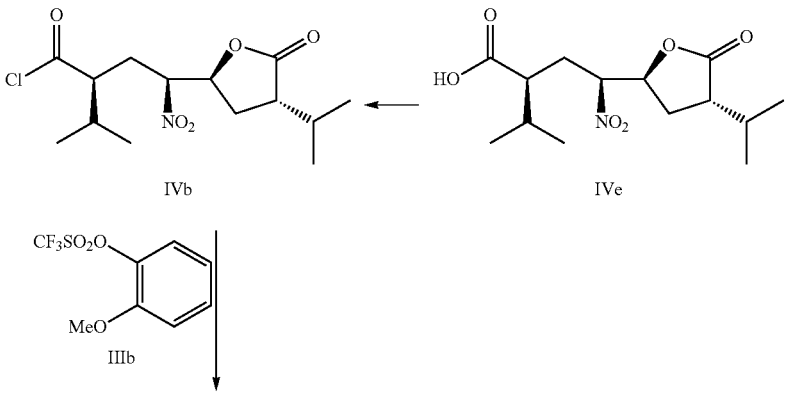

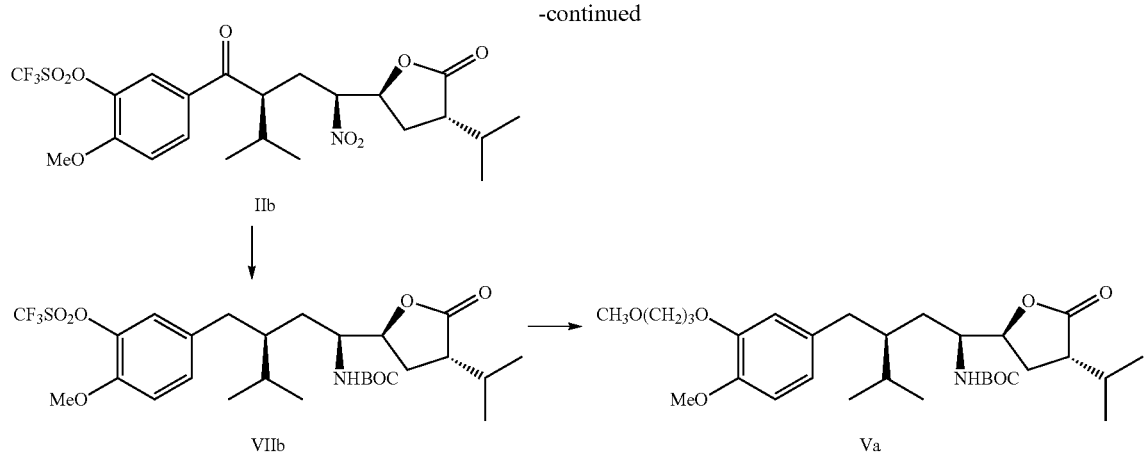

Example 7

Preparation of Acid Chloride IVb

Acid IVe (301 g, prepared as reported in US2011/0137047) was dissolved in dry acetonitrile (600 ml) and to this solution at 0° C. under inert atmosphere and stirring DMF (5 ml) and oxalyl chloride (300 g) were slowly added. Afterwards the reaction temperature was slowly increased within ca. 30 min to 40° C. and stirred at this temperature for 4 hrs. The reaction was monitored with HPLC and TLC. After completion the solvent and excess of oxalyl chloride were evaporated under reduced pressure at a bath temperature of 30° C. providing crude chloride IVb (330 g) which was directly used in the next step in Examples 8 or 9.

Example 8

Preparation of IIb from IVb and IIIb

Under inert atmosphere to a stirred solution of Guajacol triflate IIIb (256 g, prepared as reported in Tetrahedron Letters 2002, 43, 7077) in methylenechloride (1000 ml) AlCl$_3$ (280 g) was slowly added at rt. To the resulting slurry acid chloride IVb (319 g prepared in Example 7), dissolved in methylenechloride (200 ml), was slowly added that the reaction temperature remained below 30° C. (cooling!). After stirring at this temperature for 45 min the reaction mixture was heated to 40° C. for 1 hr until acid chloride IVb was consumed. The reaction was monitored by TLC and HPLC. After completion crude reaction mixture was poured slowly on ice (2.5 kg), the organic phase separated, the aqueous phase filtered and then extracted 3 times with methylenechloride (3×500 ml). The combined organic phases were washed once with water (300 ml), once with sat.-NaHCO$_3$-solution (400 ml), then with brine (400 ml), dried over sodium sulfate, filtered and the filtrate concentrated under reduced pressure. The residue was dissolved in methylenechloride (300 ml), treated with charcoal (10 g), the solution stirred for ca. 20 min, then filtered and the filtrate concentrated in vacuum providing crystalline IIb (475 g, 88% yield). This material was directly used for the next step (IIb→VIIb):

For analytical purposes a small sample of the crude material was purified by recrystallization from toluene/heptane: Anal. calculated for $C_{22}H_{28}F_3NO_9S$: C, 48.98; H, 5.23; F, 10.56; N, 2.60; O, 26.69; S, 5.94. Found: C, 48.93; H, 5.29; F, 110.50; N, 2.55; O, 26.75; S, 5.84.

Example 9

Preparation of VIIb from IVb and IIIb

Friedel-Crafts Reaction:

Under inert atmosphere to a stirred solution of Guajacol triflate (256 g, prepared as reported in Tetrahedron Letters 2002, 43, 7077) in methylenechloride (1000 ml) AlCl$_3$ (300 g) was slowly added at rt. To the resulting slurry acid chloride IVb (319 g, prepared from the corresponding acid IVc in Example 7), dissolved in methylenechloride (200 ml), was slowly added that the reaction temperature remained between 30-40° C. (cooling!). After stirring at that temperature for 60 min the reaction mixture was heated to 40° C. for 1-2 hrs until acid chloride IVb was fully consumed. The reaction was monitored by TLC and HPLC.

Afterwards crude reaction mixture was cooled to 0-5° C. and 1,1,3,3-tetramethyldisiloxane (270 g) was added and the mixture stirred at this temperature for 4-6 hrs. Reduction progress was monitored by TLC and HPLC. For work up the mixture was poured slowly on ice (3 kg). The HCl gas that evolved during this quench was scrubbed by a caustic scrubber. The organic phase was separated and the aqueous phase filtered, extracted 3 times with methylenechloride (3×500 ml). The combined organic phases were washed once with water (300 ml), once with sat.-NaHCO$_3$-solution (400 ml), then with brine (400 ml), dried over sodium sulfate, filtered and the filtrate concentrated under reduced pressure. The residue was dissolved in ethylacetate (400 ml), treated with charcoal (10 g), the solution stirred for ca. 10 min, then filtered and the filtrate concentrated under reduced pressure providing a yellows semi-crystalline intermediate, 3(S)-isopropyl-5(S)-{1(S)-nitro-3(S)-isopropyl-4-[4-methoxy-3-bromo-phenyl]-butyl}-tetrahydrofuran-2-one: 350 g (67% yield). This material was used for the reductive step:

Reduction of NO$_2$-Group and BOC-Protection:

Under inert atmosphere ZrCl$_4$ (23 g) and dry THF (800 ml) were placed in a flask. To this reddish brown solution, cooled 0° C., NaBH$_4$ (15 g) was added in portions. The color of the reaction mixture turned into pale pink. To this stirred mixture at 0° C. crude 3(S)-isopropyl-5(S)-{1(S)-nitro-3(S)-isopropyl-4-[4-methoxy-3-bromo-phenyl]-butyl}-tetrahydrofuran-2-one (52.5 g, prepared above in Example 9) in dry THF (200 ml) was added that the temperature was maintained at 0° C. After complete addition the reaction was allowed to reach rt and the stirring was continued until the reaction was completed (4 hrs). The reaction conversion was monitored by HPLC and TLC. For work up the reaction mixture was cooled to 0° C., filtered through celite, the filtrate quenched with aqueous 5%-HCl (200 ml) and the product extracted from the aqueous phase 3 times with methylenechloride (3×200 ml), the combined organic phases washed twice with brine (2×200 ml), dried with sodium sulfate (150 g), filtered, the filtrate concentrated under vacuum providing as crystalline 3(S)-isopropyl-5(S)-{1(S)-amino-3(S)-isopropyl-4-[4-methoxy-3-trifluoromethanesulfonyloxy-phenyl]-butyl}-tetrahydrofuran-2-one hydrochloride: 48 g (90% yield). This material was dissolved in methanol (200 ml), N,N-dimethyl aminopyride (0.2 g) triethylamine (22 g) and di-tert.-butyldicarbonate (30 g) were added at rt and the mixture stirred for 24 hrs to achieve complete BOC-protection of amino group. After careful acidification of the reaction mixture with glacial acetic acid (ca. 10 ml), the mixture was extracted with ethylacetate/water mixture, the organic phase separated and evaporated under reduced pressure providing crude VIIb as brawn crystalline material: 46 g (77% yield). A small sample was purified by column chromatography on silica gel. Anal. calculated for $C_{27}H_{40}F_3NO_8S$: C, 54.44; H, 6.77; F, 9.57; N, 2.35; O, 21.49; S, 5.38. Found: C, 54.50; H, 6.80; F, 9.55; N, 2.33; O, 21.40; S, 5.28.

Example 10

Preparation of VIIb from IVb and IIIb

Friedel-Crafts and reduction of 8-oxo group was carried out as described in Example 9 providing 3(S)-isopropyl-5(S)-{1(S)-nitro-3(S)-isopropyl-4-[4-methoxy-3-bromo-phenyl]-butyl}-tetrahydrofuran-2-one: 350 g (67% yield). This material was dissolved in methanol (1500 ml) and after addition of 10% Pt—C (5 g) the slurry was hydrogenated at rt under normal pressure until starting material was consumed (monitored by HPLC or TLC). The suspension was filtered through celite (20 g), to the filtrate N,N-dimethyl aminopyride (1 g), triethylamine (110 g) and di-tert.-butyldicarbonate (300 g) were added at rt and the mixture stirred for 24 hrs to achieve complete BOC-protection of the amino group. After careful acidification of the reaction mixture with glacial acetic acid (ca. 50 ml), the mixture was extracted with ethylacetate/water mixture, the organic phase separated and evaporated under reduced pressure providing crude VIIb as crystalline material: 280 g (53% yield from IVb). A small sample was purified by column chromatography on silica gel. Anal. calculated for $C_{27}H_{40}F_3NO_8S$: C, 54.44; H, 6.77; F, 9.57; N, 2.35; O, 21.49; S, 5.38. Found: C, 54.50; H, 6.80; F, 9.55; N, 2.33; O, 21.40; S, 5.28.

Example 11

Preparation of Va from VIIb

Under stirring at rt VIIb (60 g, prepared in Example 9) was dissolved in methanol (200 ml) and sodium methylate (5.5 g) was added. The solution was stirred for 30 min and evaporated under reduced pressure to dryness. The residue was taken into dried DMF (100 ml), 3-methoxy-propyl-1-chloride (20 g), NaJ (2 g) and potassium carbonate (7 g) were added and the suspension stirred at 80° C. for 4 hrs until the alkylation was completed. The reaction was monitored by HPLC or TLC. Glacial acetic acid (30 ml) was added, the reaction mixture poured on ice water (600 ml), the aqueous phase extracted 3 times with TBME (3×300 ml), the combined organic phases evaporated under reduced pressure. To the residue glacial acetic acid (100 ml) was added and the suspension stirred for ca. 1 hr at 50° C. for complete lactone formation (monitored by HPLC and TLC), then the solvent evaporated under reduced pressure providing crude Va as crystalline material: 49.5 g (92% yield). The analytical data of Va (after purification of a small sample by column chromatography) were identical as reported in e.g. WO2006/024501 on page 58, Example K) or in WO2008/119804 on page 67, Example 18 or in US2009/0076062, Example 26b and c).

Preparation of 3(S)-isopropyl-5(S)-{1(S)-tert.-butyloxycarbonyl-amino-3(S)-isopropyl-4-[4-methoxy-3-(3-methoxypropyloxy)-phenyl]-butyl}-tetrahydrofuran-2-one (Va) from 3(S)-isopropyl-5(S)-[1(S)-amino-3(S)-isopropyl-4-chloro-4-oxobutyl]-tetrahydrofuran-2-one hydrochloride (IVd) (Scheme 5)

Scheme 5

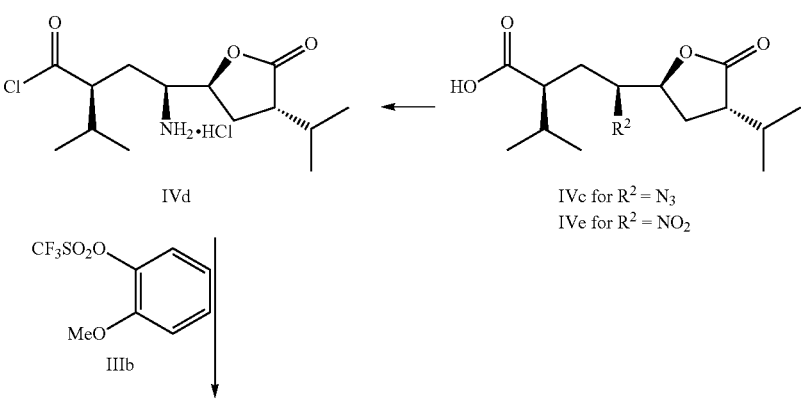

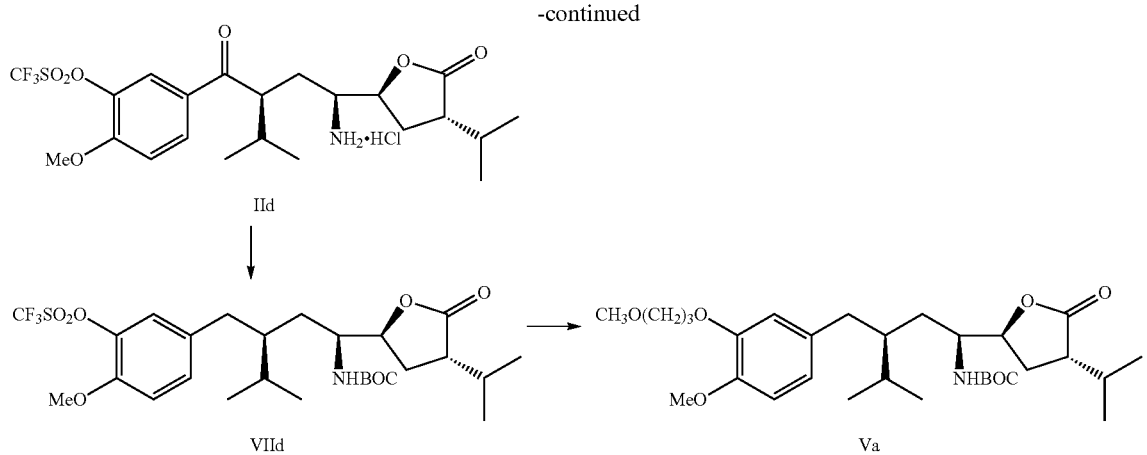

Example 12

Preparation of VIId from IVc or IVe and IIIb a) Hydrogenation of IVc or IVe:

IVe (301 g, prepared as reported in US2011/0137047) or IVc (297 g, prepared as reported in U.S. Pat. No. 5,559,111 on page 80, example 81k) was dissolved in glacial acetic acid (1000 ml) and after addition of conc.-37% HCl (105 ml) and 10%-Pd on charcoal (5 g) the reaction mixture was hydrogenated under vigorous stirring at rt until starting material either IVc or IVe was consumed. The hydrogenation was monitored by hydrogen consumption as well as with HPLC and TLC. The reaction suspension was then filtered through celite and the filtrate concentrated to dryness under reduced pressure proving crude amino acid hydrochloride.

b) Preparation of Acid Chloride IVd:

The residue from section a) was suspended into dry acetonitrile (500 ml) and to this mixture at 0° C. under inert atmosphere and stirring DMF (3 ml) and oxalyl chloride (300 g) were slowly added. Afterwards the reaction temperature was increased in ca. 30 min to 40° C. and stirred at this temperature for 4 hrs. The reaction was monitored with HPLC and TLC. After completion the solvent and excess of oxalyl chloride were evaporated under reduced pressure at a bath temperature of 30° C. providing crude chloride IVd (330 g) which was used in step c).

c) Friedel-Crafts Reaction, Reduction of 8-Oxo Group and BOC-Protection:

Under inert atmosphere to a stirred solution of Guajacol triflate IIIb (350 g) and acid chloride IVd (330 g, prepared in the above section b) in methylenechloride (1500 ml) TiCl$_4$ (600 g) was slowly added at 0° C. (ice cooling!). After addition the resulting slurry was stirred between 30-40° C. for 4 hrs until acid chloride IVd was fully consumed. The reaction was monitored by TLC and HPLC. After completion of Friedel-Crafts reaction the mixture was cooled to 0-5° C. and solution of Et$_3$SiH (350 g) in methylenechloride (500 ml) was slowly added at this temperate. After being stirred at rt over night the reduction was completed (monitored by TLC and HPLC). The mixture was poured slowly on ice water (3 kg). The organic phase was separated, the aqueous phase filtered and the filtrate extracted 3 times with methylenechloride (3×500 ml). The combined organic phases were washed once with water (300 ml), then with brine (400 ml) and dried over sodium sulfate, filtered and the filtrate concentrated under reduced pressure. The excess of qujacole triflate was removed by two extractions of the residue with toluene (2×100 ml). Afterwards the residue was dissolved in methanol (500 ml), N,N-dimethylaminopyride (1 g), triethylamine (220 g) and di-tert.-butyldicarbonate (300 g) were added at rt and the mixture stirred for 24 hrs at rt to achieve complete BOC-protection of the amino group. After careful acidification of the reaction mixture with glacial acetic acid (ca. 50 ml), the mixture was poured on water (1000 ml), the aqueous phase extracted 3 times with ethylacetate (3×300 ml) and the combined organic phases dried with sodium sulfate (300 g), filtered, the filtrate evaporated under reduced pressure providing crude VIId as semi crystalline material: 498 g (83% crude yield resp. to IVd). This material was then directly used in Example 13. For analytical purposes a small sample was purified by crystallization from acetonitrile/heptane. Anal. calculated for $C_{27}H_{40}F_3NO_8S$: C, 54.44; H, 6.77; F, 9.57; N, 2.35; O, 21.49; S, 5.38. Found: C, 54.34; H, 6.70; F, 9.50; N, 2.30; O, 21.55; S, 5.30.

Remarks:

The combination of Friedel-Crafts reaction with the reduction step can be also accomplished in methylenechloride in the presence of AlCl$_3$ followed by in situ reduction with 1,1,3,3-tetramethyldisiloxane similar as shown in Example 3.

Example 13

Preparation of Va from either VIId

Under stirring at rt VIId (498 g, from the experiment in Example 12) was dissolved in methanol (2000 ml) and sodium methylate (55 g) was added. The solution was stirred for 30 min at rt and then evaporated under reduced pressure to dryness. The residue was taken into acetonitrile (1000 ml), 3-methoxy-propylchloride (110 g) and NaJ (10 g) were added and the mixture stirred at 70° C. for 4 hrs until the alkylation was completed. The reaction was monitored by HPLC. Glacial acetic acid (100 ml) was added, the reaction mixture poured on water (3000 ml), the aqueous phase extracted 3 times with TBME (3×500 ml) and the solvents evaporated under reduced pressure. To the residue glacial acetic acid (500 ml) was added and the suspension stirred for ca. 1 hr at 30-40° C. for complete lactonization (monitored by HPLC and TLC), the solvent then evaporated under reduced pressure to dryness providing crude Va as crystalline brownish material: 430 g (80% yield). The analytical data of Va (after purification of a small sample) were identical as reported in e.g. WO2006/024501 on page 58 as Example K) or WO2008/119804 on page 67 as Example 18. or in US2009/0076062 Example 26b) and c).

Example 14

At rt under stirring VIId (50 g, from the experiment in Example 12) was dissolved in methanol (200 ml) and sodium hydroxide (12 g) was added. The solution was stirred for 30 min at rt, then 3-methoxy-1-propylchloride (20 g) and NaJ (1 g) were added and the solution stirred at 60° C. for ca. 5 hrs until the alkylation was completed. The reaction was monitored by HPLC. With addition of aqueous conc. 37%-HCl pH of the solution was carefully adjusted to 7, then acetic acid (ca. 50 ml) was added and the solution stirred for ca. 1 hr at 50° C. for finish the lactonisation process (monitored by HPLC and TLC). The reaction mixture was poured on water (1000 ml), the aqueous phase extracted 3 times with toluene (3×200 ml), the solvent dried with sodium sulfate (100 g), filtered, the filtrate concentrated under reduced pressure providing crude Va as brownish material: 40 g (75% yield). The analytical data of Va (after purification of a small sample by a column chromatography) were identical as reported in e.g. WO2006/024501 on page 58 as Example K) or WO2008/119804 on page 67 as Example 18. or in US2009/0076062 Example 26b) and c).

The invention claimed is:

1. A compound of formula II,

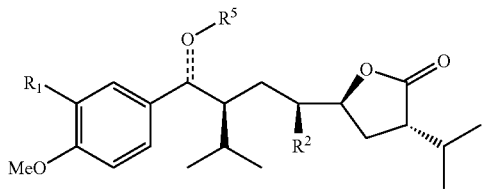

II wherein $R^1$ is halogen, preferably chlorine or bromine, alkanoyloxy, preferably acetoxy or formyloxy or trifluoroacetoxy, $FSO_2O$—, alkane-sulfonyloxy, arylalkane-sufonyloxy, arene-sulfonyloxy, arene-sulfonyloxy, preferably $CH_3SO_2O$— or Tosyloxy or $CF_3SO_2O$—, and $R^2$ is —$NO_2$ or —$N_3$, or halogen, preferably chlorine, bromine, or hydroxy or lower alkoxy or lower alkanoyloxy or alkane-sulfonyloxy-, preferably $CH_3SO_2O$—, $CF_3SO_2O$—, or —$NHR^8$, wherein $R^8$ is hydrogen, alkyl, aryl, alkylaryl, arylalkyl, preferably benzyl, mono-, di- or tri-methoxybenzyl, —C(O)alkyl, —C(O)aryl, —C(O)alkylaryl, —C(O)arylalkyl, —C(O)Oalkyl, —C(O)Oaryl, —(O)COalkylaryl, —C(O)Oarylalkyl, preferably formyl, acetyl, trifluoroacetyl, —C(O)Obenzyl (Cbz), —C(O)Otert.-butyl (BOC), and $R^5$ is either void, when the dotted lines are a double bond representing carbonyl, or $R^5$ is hydrogen, lower alkyl, preferably methyl, alkanoyl, preferably formyl or acetyl or trifluoroacetyl or —C(O)—OMe, when the dotted lines are one single bond representing sec.-alcohol, and a salt thereof.

2. The compound of formula II according to claim 1, wherein $R^1$ is chlorine, bromine, $CH_3SO_2O$—, Tosyloxy-, $CF_3SO_2O$—, and $R^2$ is —$NO_2$ or —$N_3$, or chlorine or bromine or hydroxy or lower alkanoyloxy, and $R^5$ is either void, when the dotted lines are a double bond representing carbonyl, or $R^5$ is hydrogen, lower alkanoyl, preferably acetyl or trifluoroacetyl or —C(O)—OMe, when the dotted lines are one single bond representing sec.-alcohol or a salt thereof.

3. The compound of formula II according to claim 1, wherein $R^1$ is bromine, chlorine, $CH_3SO_2O$—, Tosyloxy-, $CF_3SO_2O$—, and $R^2$ is —$N_3$ or chlorine or bromine or hydroxy, and $R^5$ is either void, when the dotted lines are a double bond representing carbonyl, or $R^5$ is hydrogen, when the dotted lines are one single bond representing sec.-alcohol, and a salt thereof.

4. The compound of formula II according to claim 1, wherein $R^1$ is bromine, chlorine, $CH_3SO_2O$—, Tosyloxy-, $CF_3SO_2O$—, and $R^2$ is bromine or chlorine or —$NHR^8$, wherein $R^8$ is hydrogen, alkyl, aryl, alkylaryl, arylalkyl, preferably benzyl, mono-, di- or tri-methoxybenzyl, or other N-protective group, in particular one which together with N forms an amide or carbamate as —C(O)alkyl, —C(O)aryl, —C(O)alkylaryl, —C(O)arylalkyl, —C(O)Oalkyl, —C(O)Oaryl, —(O)COalkylaryl, —C(O)Oarylalkyl, preferably formyl, acetyl, trifluoroacetyl, —C(O)Obenzyl (Cbz) or —C(O)Otert.-butyl (BOC), and $R^5$ is either void, when the dotted lines are a double bond representing carbonyl, or $R^5$ is hydrogen, when the dotted lines are one single bond representing sec.-alcohol, and a salt thereof.

5. The compound of formula II according to claim 1 wherein $R^1$ is halogen, preferably chlorine or bromine, $FSO_2O$—, an alkane-, arylalkane-, alkylarene-, arene-sulfonyloxy, preferably $CH_3SO_2O$— or Tosyloxy or $CF_3SO_2O$—, and $R^2$ is —$NO_2$ or —$N_3$, or —$NHR^8$, wherein $R^8$ is hydrogen, alkyl, aryl, alkylaryl, arylalkyl, preferably benzyl, mono-, di- or tri-methoxybenzyl, or other N-protective group, in particular one which together with N forms an amide or carbamate as —C(O)alkyl, —C(O)aryl, —C(O)alkylaryl, —C(O)arylalkyl, —C(O)Oalkyl, —C(O)Oaryl, —(O)COalkylaryl, —C(O)Oarylalkyl, preferably formyl, acetyl, trifluoroacetyl, —C(O)Obenzyl (Cbz), —C(O)Otert.-butyl (BOC), and $R^5$ is either void, when the dotted lines are a double bond representing carbonyl, or $R^5$ is hydrogen, lower alkyl, preferably methyl, lower alkanoyl, preferably formyl, acetyl, trifluoroacetyl, —C(O)—OMe, when the dotted lines are one single bond representing sec.-alcohol or ether or ester thereof, and a salt thereof.

6. The compound of formula II according to claim 1 wherein $R^1$ is bromine or chlorine, and $R^2$ is —$NO_2$ or —$N_3$ or —$NHR^8$, wherein $R^8$ is hydrogen, formyl, acetyl, trifluoroacetyl, —C(O)Obenzyl (Cbz), —C(O)Otert.-butyl (BOC), and $R^5$ is either void, when the dotted lines are a double bond representing carbonyl, or $R^5$ is hydrogen, when the dotted lines are one single bond representing sec.-alcohol, and a salt thereof.

7. The compound of formula II according to claim 1
wherein $R^1$ is $CH_3SO_2O$—, Tosyloxy, $CF_3SO_2O$—, and
$R^2$ is —$NO_2$ or —$N_3$ or —$NHR^8$, wherein $R^8$ is hydrogen, formyl, acetyl, trifluoroacetyl, —C(O)Obenzyl (Cbz), —C(O)Otert.-butyl (BOC), and
$R^5$ is either void, when the dotted lines are a double bond representing carbonyl, or $R^5$ is hydrogen, when the dotted lines are one single bond representing sec.-alcohol, and a salt thereof.

8. The compound of formula II according to claim 1
wherein $R^1$ is halogen, preferably chlorine or bromine, $CH_3SO_2O$—, Tosyloxy-, $CF_3SO_2O$—,
$R^2$ is —$NO_2$ or —$N_3$ or —$NHR^8$, wherein $R^8$ is hydrogen, formyl, acetyl, trifluoroacetyl, —C(O)Obenzyl (Cbz), —C(O)Otert.-butyl (BOC), and
$R^5$ is void and the dotted lines are a double bond representing carbonyl, and a salt thereof.

9. The compound of formula II according to claim 1
wherein $R^1$ is halogen, preferably chlorine or bromine, $CH_3SO_2O$—, Tosyloxy-, $CF_3SO_2O$—,
$R^2$ is —$NO_2$ or —$N_3$ or —$NHR^8$, wherein $R^8$ is hydrogen, formyl, acetyl, trifluoroacetyl, —C(O)Obenzyl (Cbz), —C(O)Otert.-butyl (BOC), and
$R^5$ is hydrogen and the dotted lines are one single bond representing sec.-alcohol, and a salt thereof.

10. The compound of formula II according to claim 1
wherein $R^1$ is halogen, preferably chlorine or bromine, $CH_3SO_2O$—, Tosyloxy-, $CF_3SO_2O$—, and
$R^2$ is —$N_3$ and
$R^5$ is void and the dotted lines are a double bond representing carbonyl, and a salt thereof.

11. The compound of formula II according to claim 1
wherein $R^1$ is halogen, preferably chlorine or bromine, $CH_3SO_2O$—, Tosyloxy, $CF_3SO_2O$—, and
$R^2$ is —$NHR^8$, wherein $R^8$ is hydrogen, formyl, acetyl, trifluoroacetyl, —C(O)Obenzyl (Cbz), —C(O)Otert.-butyl (BOC),
$R^5$ is void and the dotted lines are a double bond representing carbonyl, and a salt thereof.

12. A process for preparation of the compound of formula II, having the configuration as given in the formula,

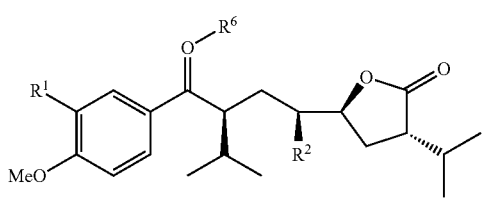

wherein $R^1$ represents halogen, preferably chlorine or bromine, alkanoyloxy, preferably acetoxy or formyloxy or trifluoracetoxy, $FSO_2O$—, and alkane-, arylalkane-, alkylarene-, arene-sulfonyloxy, preferably $CH_2SO_2O$—, Tosyloxy-, $CF_3SO_2O$—, and
$R^2$ is —$NO_2$ or —$N_3$ or —$NHR^8$, wherein $R^8$ is hydrogen, alkyl, aryl, alkylaryl, arylalkyl, —C(O)alkyl, —C(O)aryl, —C(O)alkylaryl, —C(O)arylalkyl, —C(O)Oalkyl, —C(O)Oaryl, —(O)COalkylaryl, —C(O)Oarylalkyl, preferably formyl, acetyl, trifluoroacetyl, —C(O)Obenzyl (Cbz), —C(O)Otert-butyl (BOC), and
$R^5$ is either void when the dotted lines are a double bond representing cabonyl, or $R^5$ is hydrogen, when the dotted lines are one single bond, and a salt thereof, comprising following steps:
(a) reaction of the compound of formula IV,

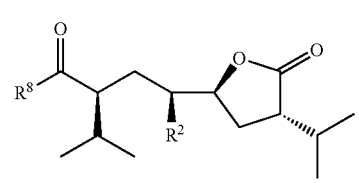

wherein $R^2$ represents —$NO_2$ or —$N_3$, or —$NHR^8$, wherein $R^8$ is hydrogen, alkyl, aryl, alkylaryl, arylalkyl, —C(O)alkyl, —C(O)aryl, —C(O)alkylaryl, —C(O)arylalkyl, —C(O)Oalkyl, —C(O)Oaryl, —(O)COalkylaryl, —C(O)Oarylalkyl, preferably formyl, acetyl, trifluoroacetyl, —C(O)Obenzyl (Cbz), —C(O)Otert-butyl (BOC), and $R^3$ is hydrogen, hydroxy, halogen, preferably chlorine or bromine, —OC(O)$R^9$ or —OC(O)O$R^9$, wherein $R^9$ is lower linear or brunched $C_{1-6}$-alkyl, preferably methyl or thyl, and a salt thereof,

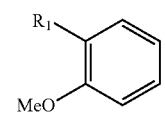

wherein $R^1$ represents halogen, preferably chlorine or bromine, lower alkanoyloxy, preferably acetoxy or formyloxy or trifluoracetoxy, $FSO_2O$— (fluorosylfonyloxy), an alkane-, arylalkane-, alkylarene-, arene-sulfonyloxy, preferably $CH_3SO_2O$— or Tosyloxy- or $CF_3SO_2O$—.

13. A process according to claim 12, wherein the compound of formula II obtained, is converted into a compound of formula V, having the configuration as given in the formula,

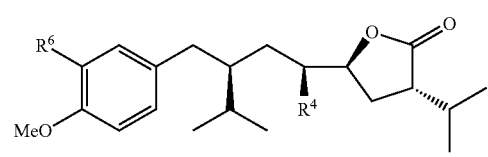

wherein $R^6$ represents hydroxy, linear or brunched $C_{1-6}$ alkoxy, $C_{1-6}$ alkoxy-$C_{1-6}$alkoxy, aryloxy, alkylaryloxy, arylalkoxy, preferably $CH_3OCH_2CH_2CH_2O$—, and $R^4$ represents —$NHR^8$, wherein $R^8$ represents hydrogen, alkyl, aryl, alkylaryl, arylalkyl, preferably benzyl, —C(O)alkyl, —C(O)aryl, —C(O)alkylaryl, —C(O)arylalkyl, —C(O)Oalkyl, —C(O)Oaryl, —(O)COalkylaryl, —C(O)Oarylalkyl, preferably formyl, acetyl, trifluoroacetyl, —C(O)Obenzyl (Cbz), —C(O)Otert.-bulyl (BOC);

comprising following steps:
a. reduction of oxo- or hydroxy-group at C(8)-atom in the compound of formula II and, when $R^2$ is $N_3$- or $NO_2$-group, reduction of $N_3$- or $NO_2$-group at C(5)-atom, in one or a few separate steps, with a reducing agent, preferably containing metal hydride or silane as reducing agent, or by homogeneous or heterogeneous hydrogenation in the presence of transition metal, preferably such as Ra—Ni, Pd, Pt or Rh, b) followed by removal of $R^6$-group and replacing it by $R^6$-group as defined in the compound of formula V, in one or more separate steps, by
  i) either direct substitution of $R^1$ group with a nucleophilic reagent $R^8$-H containing $R^6$-group such as hydroxy, linear or brunched $C_{1-6}$ alkoxy, $C_{1-6}$ alkoxy—$C_{1-6}$— alkoxy, aryloxy, alkylarloxy, arlyalkoxy, preferably $CH_3OCH_2CH_2CH_2O$—, without or in the presence of a base and a catalyst such as metal or salt thereof, preferably transition metal or salt thereof such as Cu or Pd and salt thereof,
  ii) or by selective cleavage of $R^1$ group, when $R^1$ is lower alkanoyloxy, $FSO_2O$—, an alkane-, arylalkane-, alkylarene-, arene-sulfonyloxy, preferably $CH_3SO_2O$—, Tosyloxy-, $CF_3SO_2O$—, under basic or acidic or reductive condition cleaving $R^1$ group and forming phenolic group, followed by alkylation with a suitable alkylation reagent $R^5Lvg$, wherein Lvg is a leaving group and $R^6$ is as defined for $R^6$ group, preferably by alkylation of phenol or an alkali metal salt thereof (phenolate), with $Ch_3OCH_2CH_2CH_2$-X, wherein X is chlorine or bromine,
or vice versa by first removal of $R^1$-group at C(8)-atom and $N_3$- or $NO_2$-group at C(5)-atom.

14. A process for preparation of the compound of formula V, having the configuration as given in the formula,

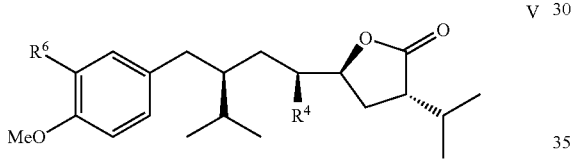

wherein $R^5$ represents hydroxy, linear or brunched $C_{1-6}$ alkoxy, $C_{1-6}$ alkoxy-$C_{1-6}$-alkoxy, aryloxy, alkylaryloxy, arylalkoxy, preferably $CH_3OCH_2CH_2CH_2O$—, and $R^4$ represents —$NHR^5$, wherein $R^5$ represents hydrogen, alkyl, aryl, alklaryl, arylalkyl, preferably benzyl, —C(O)alkyl, —C(O)aryl, —C(O)alkylaryl, —C(O)arylalkyl, —C(O)Oalkyl, —C(O)aryl, —(O)COalkylaryl, —C(O)Oarylalkyl, preferably formyl, acetyl, trifluoroacetyl, —C(O)Obenzyl (Cbz), —C(O)Otert.-butyl (BOC),
comprising following steps:
a) reaction of the compound of formula IV,

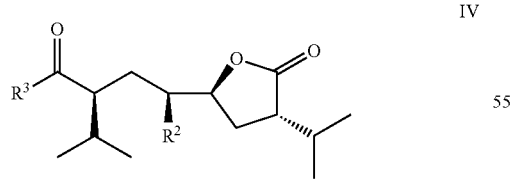

wherein $R^2$ represents —$NO_2$ or —$N_3$, or $NHR^8$, wherein $R^8$ is hydrogen, alkyl, aryl, alkylaryl, arulalkyl, preferably benzyl, —C(O)alkyl, —C(O)aryl, —C(O)alkylaryl, —C(O)arylalkyl, —C(O)Oalkyl, —C(O)Oaryl, —(O)COalkylaryl, —C(O)Oarylalkyl, preferably formyl, acetyl, trifluoroacetyl, —C(O)Obenzyl (Cbz), —C(O)Otert-butyl (BOC), and $R^8$ is hydrogen or hydroxy or halogen, preferably chlorine, bromine, or —OC(O)$R^9$ or —OC(O)O$R^9$, wherein $R^9$ is lower linear or brunched $C_{1-6}$-alkyl, preferably methyl or ethyl or tert.-butyl, and a salt thereof,
with a compound of formula III,

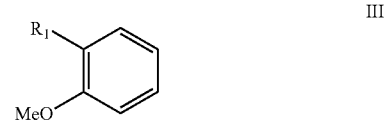

wherein $R^1$ represents halogen, preferably chlorine or bromine, alkanoyloxy, preferably acetoxy, formyloxy, triflouracetoxy, $FSO_2O$— (fluorosulfonyloxy), an alkane-, arylalkane-, alkylarene-, arene-sulfonyloxy, preferably $CH_3SO_2O$— or Tosyloxy- or $CF_3SO_2O$—,
under Friedel-Crafts condition in the presence of a suitable catalyst used for Friedel-Crafts reaction such as bortrifluoroetherate, $HN(SO_2CF_3)_2$, metal salt, preferably Al-, Ri-, Zn-, Zr-, Bi-, lanthanide-halide or triflate, providing compound formula II,

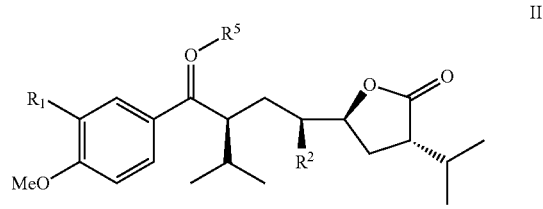

wherein $R^1$ is the same as defined in compound of formula III, $R^2$ is as defined in compound of formula IV,
$R^5$ is either void when the dotted lines are a double bond representing carbonyl, or $R^5$ is hydrogen, when the dotted lines are one single bond representing a sec.-alcohol:
b) reduction of oxo- or hydroxy-group at C(8)-atom and $N_3$— or $NO_2$—group at C(5)-atom, where $R^2$ is $N_3$— or $NO_2$—group as defined in the compound of formula II, in one or in a few separate steps, with a reducing agent, preferably containing metal hydride or silane as reducing agent, or by homogeneous or heterogeneous hydrogenalion in the presence of transition metal, preferably such as Ra-Ni, Pd, Pt or Rh,
followed by removal of $R^3$-group and replacing it by $R^6$-group as defined in the compound of formula V, in one or more separate steps, by
  i) either direct substitution of $R^1$ group with a nucleophilic reagent $R^6$-H containing $R^6$-group such as hydroxy, linear or brunched $C_{1-6}$ alkoxy, $C_{1-6}$ alkoxy-$C_{1-6}$- alkoxy, aryloxy, alkylaryloxy, arylalkoxy, preferably $CH_3OCH_2CH_2CH_2O^-$, without or in the presence of a catalyst such as metal or salt thereof, preferably transition metal or salt thereof such as Cu or Pd and salt thereof,
  ii) or by selective cleavage of $R^3$ group, when $R^1$ is alkanoyloxy, an alkane-, arylalkane-, alkylarene-, arene- sulfonyloxy, preferably $CH_3SO_2O$—, Tosyloxy-, $CF_3SO_2O$—, under basic or acidic or reductive condition cleaving $R^1$ group and forming phenolic group followed by alkylation thereof with a suitable alkylation reagent defined as $R^6$-Lvg, wherein Lvg is a leaving group and $R^6$ is group defined, preferably by alkylation of phenolic group, or an alkali metal salt thereof such as phenolate, with $CH_3OCH_2CH_2CH_2$-X, wherein X is chlorine or bromine,
or vice versa by first removal of $R^1$ group and replacing it by $R^6$-group followed by reduction of oxo- or hydroxy-group at C(8)-atom and $N_3$— or $NO_2$—group at C(5)-atom.

15. A process according to anyone of claims 12-14, wherein in the compounds of formulas II, III, IV, V and VI
$R^1$ represents chlorine or bromine,
$R^2$ represents $N_3$,
$R^3$ represents chlorine,
$R^4$ represents $NHR^8$, wherein $R^8$ is hydrogen, acetyl, trifluoroacetyl, —C(O)Obenzyl (Cbz), —C(O)Otert.-butyl (BOC),
$R^5$ is void and the dotted lines are a double bond representing carbonyl, and
$R^6$ is $CH_3OCH_2CH_2CH_2O$—, and
$R^1$ group in compound of formula VII was replaced by direct substitution of $R^3$ group with $CH_3OCH_2CH_2CH_2O$— group by treatment with $CH_3OCH_2CH_2CH_2OH$ in the presence of a base and catalyst such as Cu- or Pd-salt.

16. A process according to anyone of claims 12-14, wherein in the compounds of formulas II, III, IV, V and VII
$R^1$ represents chlorine or bromine,
$R^2$ represents —$NH_3^+Cl^-$ or $NHR^8$ is acetyl, trifluoroacetyl, —C(O)OMe, —C(O)Obenzyl (Cbz), —C(O)Otert.-butyl (BOC), and
$R^3$ represents chlorine,
$R^4$ represents $NHR^8$, wherein $R^8$ represents hydrogen, acetyl, trifluoroacetyl, —C(O)OMe, —C(O)Obenzyl (Cbz), —C(O)Otert-butyl (BOC),
$R^5$ is void and the dotted lines are a double bone representing carbonyl, and
$R^6$ is $CH_3OCH_2CH_2CH_2O$— and
$R^1$ group in compound of formula VII was replaced by direct substitution of $R^1$ group with $CH_2OCH_2CH_2CH_2O^-$ by treatment with $CH_2OCH_2CH_2CH_2OH$ in the presence of a base and catalyst such as Cu- or Pd- salt.

17. A process according to anyone of claim 12-14, wherein in the compounds of formulas II, III, IV, V and VII
$R^1$ represents $CH_3SO_2O$—, Tosyloxy-, $CF_3SO_2O$—,
$R^2$ represents $NH_3^+Cl^-$ or $NHR^8$, wherein $R^8$ is acetyl, trifluoroacetyl, —C(O)OMe, —C(O)Obenzyl (Cbz), —C(O)Otert.-butyl (BOC), and
$R^3$ represents chlorine,
$R^4$ represents $NHR^8$, wherein $R^8$ represents hydrogen, acetyl, trifluoroacetyl, —C(O)OMe, —C(O)Obenzyl (Cbz), —C(O)Otert-butyl (BOC),
$R^5$ is void and the dotted lines are a double bond representing crabonyl, and
$R^8$ is $CH_3OCH_2CH_2CH_2O$—, and
$R^1$ group in the compound of formula VII was removed by selective cleavage of $R^1$ group under basic condition forming phenolic group, followed by alkylation of alkali metal phenolate with $CH_3OCH_2CH_2CH_2$—X, wherein X is chlorine or bromine.

18. A process according to anyone of claims 12-14, wherein in the compounds of formulas II, III, IV, V and VII
$R^1$ represents chlorine or bromine,
$R^2$ represents $N_3$ or $NO_2$ or —$NH_2^+Cl^-$ or $NHR^8$, wherein $R^8$ is acetyl, trifluoroacetyl, —C(O)OMe, —C(O)Obenzyl (Cbz), —C(O)Otert-butyl (BOC),
$R^3$ represents chlorine,
$R^4$ represents $NHR^8$, wherein $R^8$ represents hydrogen, acetyl, trifluoroacetyl, —C(O)Obenzyl (Cbz), —C(O)Otert.-butyl (BOC),
$R^5$ is hydrogen and the dotted lines are one single bond representing sec.-alcohol, and
$R^6$ is $CH_3OCH_2CH_2CH_2O$—, and
$R^1$ group in compound of formula II was replaced by direct substitution of $R^1$ group with $CH_3OCH_2CH_2CH_2O$— by treatment with $CH_3OCH_2CH_2CH_2OH$ in the presence of a base and catalyst such as Cu or Pd-salt.

19. A process according to anyone of claims 12-14, wherein in the compounds of formulas II, III, IV, V and VII
$R^1$ represents $CH_3SO_2O$—, Tosyloxy or $CF_3SO_2O$—,
$R^2$ represents $N_3$,
$R^3$ represents chlorine,
$R^4$ represents $NHR^8$, wherein $R^8$ represents hydrogen, acetyl, trifluoroacetyl, —C(O)Obenzyl (Cbz), —C(O)Otert.-butyl (BOC),
$R^5$ is void and the dotted lines are a double bond representing carbonyl, and
$R^6$ is $CH_3OCH_2CH_2CH_2O$—, and
$R^1$ group in the compound of formula VII was removed by selective cleavage of $R^1$ group under basic condition forming phenolic group, followed by alkylation of alkali metal phenolate with $CH_3OCH_2CH_2CH_2$—X, wherein X is chlorine or bromine.

20. A process according to anyone of claim 12-14, wherein in the compounds of formulas II, III, IV, V and VII
$R^1$ represents $CH_3SO_2O$—, Tosyloxy and $CF_3SO_2O$—,
$R^2$ represents $N_3$ or $NO_2$ or $NH_3^+Cl^-$ or $NHR^8$, wherein $R^8$ is acetyl, trifluoroacetyl, —C(O)OMe, —C(O)Obenzyl (Cbz), —C(O)Otert-butyl (BOC),
$R^3$ represents chlorine,
$R^4$ represents $NHR^8$, wherein $R^8$ represents hydrogen, acetyl, trifluoroacetyl, —C(O)Obenzyl (Cbz), —C(O)Otert.-butyl (BOC),
$R^5$ is hydrogen and the dotted lines are one single bond representing a sec.-alcohol, and
$R^6$ is $CH_3OCH_2CH_2CH_2O$—, and
$R^1$ group in the compound of formula VII was removed by selective cleavage of $R^1$ group under basic condition forming phenolic group, followed by alkylation of alkali metal phenolate with $CH_3OCH_2CH_2CH_2$—X, wherein X is chlorine or bromine.

* * * * *